US007186537B2

(12) United States Patent
Dai

(10) Patent No.: US 7,186,537 B2
(45) Date of Patent: Mar. 6, 2007

(54) HUMAN GAK-RELATED GENE VARIANTS ASSOCIATED WITH LUNG CANCER

(76) Inventor: Ken-Shwo Dai, 1F., No.18, Industry E. Rd., IV, Science-Based Industrial, Science-Based Industrial Park, Hsinchu (TW)

( * ) Notice: Subject to any disclaimer, the term of this patent is extended or adjusted under 35 U.S.C. 154(b) by 0 days.

(21) Appl. No.: 11/208,877

(22) Filed: Aug. 22, 2005

(65) Prior Publication Data

US 2006/0063215 A1 Mar. 23, 2006

Related U.S. Application Data

(62) Division of application No. 10/102,549, filed on Mar. 20, 2002, now Pat. No. 6,953,669.

(51) Int. Cl.

| | |
|---|---|
| ***C12N 9/12*** | (2006.01) |
| ***C12N 15/00*** | (2006.01) |
| ***C12N 1/20*** | (2006.01) |
| ***C07H 21/04*** | (2006.01) |
| ***C12P 21/06*** | (2006.01) |

(52) U.S. Cl. .................. 435/194; 536/23.2; 435/320.1; 435/252.3; 435/69.1

(58) Field of Classification Search .................... 435/7, 435/4, 7.1, 7.23, 320.1, 252.33, 325, 194, 435/252.1, 69.1; 536/23.5, 23.1, 23.2
See application file for complete search history.

(56) References Cited

OTHER PUBLICATIONS

Sethi, T. "Science, medicine, and the future: Lung cancer" *BMJ*, 314 (7081): 652, (1997).

Kanaoka, Y., et al. "GAK: a cyclin G associated kinase contains a tensin/auxilin-like domain" *FEBS Letters*, vol. 402, p. 73-80, (1997).

Reimer, C.L., et al. "Altered Regulation of Cyclin G in Human Breast Cancer and Its Specific Localization at Replication Foci . . . Cells" *J. of Bio. Chem.*, vol. 274, No. 16, p. 11022-11029, (1999).

Keyomarsi, K., et al. "Redundant cyclin overexpression and gene amplification in breast cancer cells" *Proc. Natl. Acad. Sci. USA*, vol. 90, p. 1112-1116, (1993).

Horne, M.C., et al. "Cyclin G1 and Cyclin G2 Comprise a New Family of Cyclins with Contrasting Tissue-specific and Cell . . . Expression" *J. of Bio. Chem.*, vol. 271, No. 11, p. 6050-6061, (1996).

Kimura, S.H., et al., "Structure, Expression, and Chromosomal Localization of Human GAK" *Genomics*, vol. 44, p. 179-187, (1997).

Michelland, S., et al. "Comparison of Chromosomal Imbalances in Neuroendocrine and Non-Small-Cell Lung Carcinomas" *Cancer Genet Cytogenet*, vol. 114, p. 22-30, (1999).

"On the preparation and utilization of isolated and purified oligonucleotides" [electronic resource], Andrew Chin, allegedly deposited in UNC library on Mar. 14, 2002, date of publication, if any, is in question.

*Primary Examiner*—Rebecca E. Prouty
*Assistant Examiner*—Malgorzata Walicka
(74) *Attorney, Agent, or Firm*—Ladas and Parry LLP

(57) ABSTRACT

The invention relates to the nucleic acid and polypeptide sequences of two novel human GAK-related gene variants.

The invention also relates to the process for producing the polypeptides of the variants.

The invention further relates to the use of the nucleic acid and polypeptide sequences of the gene variants in diagnosing diseases associated with the deficiency of GAK gene, in particular, iron homeostasis impairment-related diseases or non-small cell lung cancer (NSCLC), e.g. large cell lung cancer.

4 Claims, 29 Drawing Sheets

FIG. 1A

```
AGCCACCGCCATGTCGCTGCTGCAGTCTGCGCTCGACTTCTTGGCGGGTCCAGGCTCCCT - 60
          M  S  L  L  Q  S  A  L  D  F  L  A  G  P  G  S  L  -17
GGGCGGTGCTTCCGGCCGCGACCAGAGTGACTTCGTGGGCAGACGGTGGAACTGGGCGA - 120
 G  G  A  S  G  R  D  Q  S  D  F  V  G  Q  T  V  E  L  G  E  -37
GCTGCGGCTGCGGGTGCGGCGGGTCCTGGCCGAAGGAGGGTTTGCATTTGTGTATGAAGC - 180
 L  R  L  R  V  R  R  V  L  A  E  G  G  F  A  F  V  Y  E  A  -57
TCAAGATGTGGGGAGTGGCAGAGAGTATGCATTAAAGAGGCTATTATCCAATGAAGAGGA - 240
 Q  D  V  G  S  G  R  E  Y  A  L  K  R  L  L  S  N  E  E  E  -77
AAAGAACAGAGCCATCATTCAAGAAGTTTGCTTCATGAAAAAGCTTTCCGGCCACCCGAA - 300
 K  N  R  A  I  I  Q  E  V  C  F  M  K  K  L  S  G  H  P  N  -97
CATTGTCCAGTTTTGTTCTGCAGCGTCTATAGGAAAAGAGGAGTCAGACACGGGGCAGGC - 360
 I  V  Q  F  C  S  A  A  S  I  G  K  E  E  S  D  T  G  Q  A  -117
TGAGTTCCTCTTGCTCACAGAGCTCTGTAAAGGGCAGCTGGTGGAATTTTTGAAGAAAAT - 420
 E  F  L  L  L  T  E  L  C  K  G  Q  L  V  E  F  L  K  K  M  -137
GGAATCTCGAGGCCCCCTTTCGTGCGACACGGTTCTGAAGATCTTCTACCAGACGTGCCG - 480
 E  S  R  G  P  L  S  C  D  T  V  L  K  I  F  Y  Q  T  C  R  -157
CGCCGTGCAGCACATGCACCGGCAGAAGCCGCCCATCATCCACAGGGACCTCAAGGTTGA - 540
 A  V  Q  H  M  H  R  Q  K  P  P  I  I  H  R  D  L  K  V  E  -177
GAACTTGTTGCTTAGTAACCAAGGGACCATTAAGCTGTGTGACTTTGGCAGTGCCACGAC - 600
 N  L  L  L  S  N  Q  G  T  I  K  L  C  D  F  G  S  A  T  T  -197
CATCTCGCACTACCCTGACTACAGCTGGAGCGCCCAGAGGCGAGCCCTGGTGGAGGAAGA - 660
 I  S  H  Y  P  D  Y  S  W  S  A  Q  R  R  A  L  V  E  E  E  -217
```

FIG. 1B

```
GATCACGAGGAATACAACACCAATGTATAGAACACCAGAAATCATAGACTTGTATTCCAA - 720
 I  T  R  N  T  T  P  M  Y  R  T  P  E  I  I  D  L  Y  S  N   -237
CTTCCCGATCGGCGAGAAGCAGGATATCTGGGCCCTGGGCTGCATCTTGTACCTGCTGTG - 780
 F  P  I  G  E  K  Q  D  I  W  A  L  G  C  I  L  Y  L  L  C   -257
CTTCCGGCAGCACCCTTTTGAGGATGGAGCGAAACTTCGAATAGTCAATGGGAAGTACTC - 840
 F  R  Q  H  P  F  E  D  G  A  K  L  R  I  V  N  G  K  Y  S   -277
GATCCCCCCGCACGACACGCAGTACACGGTCTTCCACAGCCTCATCCGCGCCATGCTGCA - 900
 I  P  P  H  D  T  Q  Y  T  V  F  H  S  L  I  R  A  M  L  Q   -297
GGTGAACCCGGAGGAGCGGCTGTCCATCGCCGAGGTGGTGCACCAGCTGCAGGAGATCGC - 960
 V  N  P  E  E  R  L  S  I  A  E  V  V  H  Q  L  Q  E  I  A   -317
GGCCGCCCGCAACGTGAACCCCAAGTCTCCCATCACAGAGCTCCTGGAGCAGAATGGAGG - 1020
 A  A  R  N  V  N  P  K  S  P  I  T  E  L  L  E  Q  N  G  G   -337
CTACGGGAGCGCCACACTGTCCCGAGGGCCACCCCCTCCCGTGGGCCCCGCTGGCAGTGG - 1080
 Y  G  S  A  T  L  S  R  G  P  P  P  P  V  G  P  A  G  S  G   -357
CTACAGTGGAGGCCTGGCGCTGGCGGAGTACGACCAGCCGTATGGCGGCTTCCTGGACAT - 1140
 Y  S  G  G  L  A  L  A  E  Y  D  Q  P  Y  G  G  F  L  D  I   -377
TCTGCGGGGTGGGACAGAGCGGCTCTTCACCAACCTCAAGGACACCTCCTCCAAGGTCAT - 1200
 L  R  G  G  T  E  R  L  F  T  N  L  K  D  T  S  S  K  V  I   -397
CCAGTCCGTCGCTAATTATGCAAAGGGTGACCTGGACATATCTTACATCACATCCAGAAT - 1260
 Q  S  V  A  N  Y  A  K  G  D  L  D  I  S  Y  I  T  S  R  I   -417
TGCAGTGATGTCATTCCCAGCAGAAGGTGTGGAGTCAGCGCTCAAAAACAACATCGAAGA - 1320
 A  V  M  S  F  P  A  E  G  V  E  S  A  L  K  N  N  I  E  D   -437
```

FIG. 1C

```
TGTGCGGTTGTTCCTGGACTCCAAGCACCCAGGGCACTATGCCGTCTACAACCTGTCCCC - 1380
 V  R  L  F  L  D  S  K  H  P  G  H  Y  A  V  Y  N  L  S  P   -457
GAGGACCTACCGGCCCTCCAGGTTCCACAACCGGGTCTCCGAGTGTGGCTGGGCAGCACG - 1440
 R  T  Y  R  P  S  R  F  H  N  R  V  S  E  C  G  W  A  A  R   -477
GCGGGCCCCACACCTGCACACCCTGTACAACATCTGCAGGAACATGCACGCCTGGCTGCG - 1500
 R  A  P  H  L  H  T  L  Y  N  I  C  R  N  M  H  A  W  L  R   -497
GCAGGACCACAAGAACGTCTGCGTCGTGCACTGCATGGACGGGAGAGCCGCGTCTGCTGT - 1560
 Q  D  H  K  N  V  C  V  V  H  C  M  D  G  R  A  A  S  A  V   -517
GGCCGTCTGCTCCTTCCTGTGCTTCTGCCGTCTCTTCAGCACCGCGGAGGCCGCCGTGTA - 1620
 A  V  C  S  F  L  C  F  C  R  L  F  S  T  A  E  A  A  V  Y   -537
CATGTTCAGCATGAAGCGCTGCCCACCAGGCATCTGGCCATCCCACAAAAGGTACATCGA - 1680
 M  F  S  M  K  R  C  P  P  G  I  W  P  S  H  K  R  Y  I  E   -557
GTACATGTGTGACATGGTGGCGGAGGAGCCCATCACACCCCACAGCAAGCCCATCCTGGT - 1740
 Y  M  C  D  M  V  A  E  E  P  I  T  P  H  S  K  P  I  L  V   -577
GAGGGCCGTGGTCATGACACCCGTGCCGCTGTTCAGCAAGCAGAGGAGCGGCTGCAGGCC - 1800
 R  A  V  V  M  T  P  V  P  L  F  S  K  Q  R  S  G  C  R  P   -597
CTTCTGCGAGGTCTACGTGGGGGACGAGCGTGTGGCCAGCACCTCCCAGGAGTACGACAA - 1860
 F  C  E  V  Y  V  G  D  E  R  V  A  S  T  S  Q  E  Y  D  K   -617
GATGCGGGACTTTAAGATTGAAGATGGCAAAGCGGTGATTCCCCTGGGCGTCACGGTGCA - 1920
 M  R  D  F  K  I  E  D  G  K  A  V  I  P  L  G  V  T  V  Q   -637
AGGAGACGTGCTCATCGTCATCTATCACGCCCGGTCCACTCTGGGCGGCCGGCTGCAGGC - 1980
 G  D  V  L  I  V  I  Y  H  A  R  S  T  L  G  G  R  L  Q  A   -657
CAAGATGGCATCCATGAAGATGTTCCAGATTCAGTTCCACACGGGGTTTGTGCCTCGGAA - 2040
 K  M  A  S  M  K  M  F  Q  I  Q  F  H  T  G  F  V  P  R  N   -677
```

FIG. 1D

```
CGCCACCACTGTGAAATTTGCCAAGTATGACCTGGACGCGTGTGACATTCAAGAAAAATA - 2100
 A  T  T  V  K  F  A  K  Y  D  L  D  A  C  D  I  Q  E  K  Y   -697
CCCGGATTTATTTCAAGTGAACCTGGAAGTGGAGGTGGAGCCCAGGGACAGGCCGAGCCG - 2160
 P  D  L  F  Q  V  N  L  E  V  E  V  E  P  R  D  R  P  S  R   -717
GGAAGCCCCACCATGGGAGAACTCGAGCATGAGGGGCTGAACCCCAAAATCCTGTTTTC - 2220
 E  A  P  P  W  E  N  S  S  M  R  G  L  N  P  K  I  L  F  S   -737
CAGCCGGGAGGAGCAGCAAGACATTCTGTCTAAGTTTGGGAAGCCGGAGCTTCCCCGGCA - 2280
 S  R  E  E  Q  Q  D  I  L  S  K  F  G  K  P  E  L  P  R  Q   -757
GCCTGGCTCCACGGCTCAGTATGATGCTGGGGCAGGGTCCCCGGAAGCCGAACCCACAGA - 2340
 P  G  S  T  A  Q  Y  D  A  G  A  G  S  P  E  A  E  P  T  D   -777
CTCTGACTCACCGCCAAGCAGCAGCGCGGACGCCAGTCGCTTCCTGCACACGCTGGACTG - 2400
 S  D  S  P  P  S  S  S  A  D  A  S  R  F  L  H  T  L  D  W   -797
GCAGGAAGAGAAGGAGGCAGAGACTGGTGCAGAAAATGCCTCTTCCAAGGAGAGCGAGTC - 2460
 Q  E  E  K  E  A  E  T  G  A  E  N  A  S  S  K  E  S  E  S   -817
TGCCCTGATGGAGGACAGAGACGAGAGTGAGGTGTCAGATGAAGGGGATCCCCGATCTC - 2520
 A  L  M  E  D  R  D  E  S  E  V  S  D  E  G  G  S  P  I  S   -837
CAGCGAGGGCCAGGAACCCAGGGCCGACCCAGAGCCCCCCGGCCTGGCAGCAGGGCTGGT - 2580
 S  E  G  Q  E  P  R  A  D  P  E  P  P  G  L  A  A  G  L  V   -857
GCAGCAGGACTTGGTTTTTGAGGTGGAGACACCGGCTGTGCTGCCAGAGCCTGTGCCACA - 2640
 Q  Q  D  L  V  F  E  V  E  T  P  A  V  L  P  E  P  V  P  Q   -877
GGAAGACGGGGTCGACCTCCTGGGCCTGCACTCCGAGGTGGGCGCAGGGCCAGCTGTACC - 2700
 E  D  G  V  D  L  L  G  L  H  S  E  V  G  A  G  P  A  V  P   -897
CCCGCAGGCCTGCAAGGCCCCCTCCAGCAACACCGACCTGCTCAGCTGCCTCCTTGGCC - 2760
 P  Q  A  C  K  A  P  S  S  N  T  D  L  L  S  C  L  L  G  P   -917
```

FIG. 1E

```
CCCTGAGGCCGCCTCCCAGGGGCCCCGGAGGATCTGCTCAGCGAGGACCCGCTGCTCCT - 2820
 P  E  A  A  S  Q  G  P  P  E  D  L  L  S  E  D  P  L  L  L   -937
GGCAAGCCCGGCCCCTCCCCTGAGCGTGCAGAGCACCCCAAGAGGAGGCCCCCTGCCGC - 2880
 A  S  P  A  P  P  L  S  V  Q  S  T  P  R  G  G  P  P  A  A   -957
TGGCAACAACTCCCAGCCCTGCTCCAATCCTGATCTCTTCGGCGAATTTCTCAATTCGGA - 2940
 G  N  N  S  Q  P  C  S  N  P  D  L  F  G  E  F  L  N  S  D   -977
CTCTGTGACCGTCCCACCATCCTTCCCGTCTGCCCACAGCGCTCCGCCCCCATCCTGCAG - 3000
 S  V  T  V  P  P  S  F  P  S  A  H  S  A  P  P  P  S  C  S   -997
CGCCGACTTCCTGCACCTGGGGGATCTGCCAGGAGAGCCCAGCAAGATGACAGCCTCGTC - 3060
 A  D  F  L  H  L  G  D  L  P  G  E  P  S  K  M  T  A  S  S  -1017
CAGCAACCCAGACCTGCTGGGAGGATGGGCTGCCTGGACCGAGACTGCAGCGTCGGCAGT - 3120
 S  N  P  D  L  L  G  G  W  A  A  W  T  E  T  A  A  S  A  V  -1037
GGCCCCCACGCCAGCCACAGAAGGCCCCCTCTTCTCTCCTGGAGGTCAGCCGGCCCCTTG - 3180
 A  P  T  P  A  T  E  G  P  L  F  S  P  G  G  Q  P  A  P  C  -1057
TGGCTCTCAGGCCAGCTGGACCAAGTCTCAGAACCCGGACCCATTTGCTGACCTTGGCGA - 3240
 G  S  Q  A  S  W  T  K  S  Q  N  P  D  P  F  A  D  L  G  D  -1077
CCTCAGCTCCGGCCTCCAAGGCTCACCAGCTGGATTTCCTCCTGGGGGCTTCATTCCCAA - 3300
 L  S  S  G  L  Q  G  S  P  A  G  F  P  P  G  G  F  I  P  K  -1097
AACGGCCACCACGGCCAAAGGCAGCAGCTCCTGGCAGACAAGTCGGCCGCCAGCCCAGGG - 3360
 T  A  T  T  A  K  G  S  S  S  W  Q  T  S  R  P  P  A  Q  G  -1117
CGCCTCATGGCCCCCTCAGGCCAAGCCGCCCCCCAAAGCCTGCACACAGCCAAGGCCTAA - 3420
 A  S  W  P  P  Q  A  K  P  P  P  K  A  C  T  Q  P  R  P  N  -1137
CTATGCCTCGAACTTCAGTGTGATCGGGGCGCGGGAGGAGCGGGGGGTCCGCGCACCCAG - 3480
 Y  A  S  N  F  S  V  I  G  A  R  E  E  R  G  V  R  A  P  S  -1157
```

FIG. 1F

```
CTTTGCTCAAAAGCCAAAAGTCTCTGAGAACGACTTTGAAGATCTGTTGTCCAATCAAGG - 3540
 F  A  Q  K  P  K  V  S  E  N  D  F  E  D  L  L  S  N  Q  G   -1177
CTTCTCCTCCAGGTCTGACAAGAAAGGGCCAAAGACCATTGCAGAGATGAGGAAGCAGGA - 3600
 F  S  S  R  S  D  K  K  G  P  K  T  I  A  E  M  R  K  Q  D   -1197
CCTGGCTAAAGACACGGACCCACTCAAGCTGAAGCTCCTGGACTGGATTGAGGGCAAGGA - 3660
 L  A  K  D  T  D  P  L  K  L  K  L  L  D  W  I  E  G  K  E   -1217
GCGGAACATCCGGGCCCTGCTGTCCACGCTGCACACAGTGCTGTGGGACGGGGAGAGCCG - 3720
 R  N  I  R  A  L  L  S  T  L  H  T  V  L  W  D  G  E  S  R   -1237
CTGGACGCCCGTGGGCATGGCCGACCTGGTGGCTCCGGAGCAAGTGAAGAAGCACTATCG - 3780
 W  T  P  V  G  M  A  D  L  V  A  P  E  Q  V  K  K  H  Y  R   -1257
CCGCGCGGTGCTGGCCGTGCACCCCGACAAGGCTGCGGGGCAGCCGTACGAGCAGCACGC - 3840
 R  A  V  L  A  V  H  P  D  K  A  A  G  Q  P  Y  E  Q  H  A   -1277
CAAGATGATCTTCATGGAGCTGAATGACGCCTGGTCGGAGTTTGAGAACCAGGGCTCCCG - 3900
 K  M  I  F  M  E  L  N  D  A  W  S  E  F  E  N  Q  G  S  R   -1297
GCCCCTCTTCTGAGGCCGCAGTGGTGGTGGCTGCGCACACAGCTCCACAGGTTGGGAGCC - 3960
 P  L  F  *                                                   - 1300
GTCGTGGGACCTGGGTCCCCACCGTGAGGACCCCGTGGGCGACAGCAGGTGTGGCCAGGG - 4020
TGGGGCTCCGAGCCCCGGGTCACCGCCCGCCCAGCGTTCCAGGCACATGAAGAGAAAGCA - 4080
TTCCAAAGCCTCTGATTGTTGTTTCCTTTTTCTCCTCCCGAAGGAACAGCTGATTCATGC - 4140
TCCTCCCGCAATTGTCACGTCTGTGATTTATTTGGTGTTTCGGGCGTGGCCTCTGGAGCC - 4200
CCGGCACGTGGTGGGCCACGCTGCTGGCGCTCATGGGCCCTGGTGTTTGCACCGCACTTT - 4260
GTAATCAGTCCCGTGGTTGTCTGTACAGAATTAAACTATTTTCCGATG - 4308
```

FIG. 2A

```
GGGCCGGCGGTTGCTGAGCTGACCCGGACGGCGAGGGAGCGGGAGCCCGAGCCCGACCAC - 60
TCCGGCTGCCGCGGGGTGCGGCGCAGCCACCGCCATGTCGCTGCTGCAGTCTGCGCTCGA - 120
                                    M  S  L  L  Q  S  A  L  D   -9
CTTCTTGGCGGGTCCAGGCTCCCTGGGCGGTGCTTCCGGCCGCGACCAGAGTGACTTCGT - 180
 F  L  A  G  P  G  S  L  G  G  A  S  G  R  D  Q  S  D  F  V   -29
GGGGCAGACGGTGGAACTGGGCGAGCTGCGGCTGCTCCTGGCAAGCCCGGCCCCTCCCCT - 240
 G  Q  T  V  E  L  G  E  L  R  L  L  L  A  S  P  A  P  P  L   -49
GAGCGTGCAGAGCACCCCAAGAGGAGGGCCCCCTGCCGCTGCTGACCCCTTTGGCCCGCT - 300
 S  V  Q  S  T  P  R  G  G  P  P  A  A  A  D  P  F  G  P  L   -69
TCTGCCGTCTTCAGGCAACAACTCCCAGCCCTGCTCCAATCCTGATCTCTTCGGCGAATT - 360
 L  P  S  S  G  N  N  S  Q  P  C  S  N  P  D  L  F  G  E  F   -89
TCTCAATTCGGACTCTGTGACCGTCCCACCATCCTTCCCGTCTGCCCACAGCGCTCCGCC - 420
 L  N  S  D  S  V  T  V  P  P  S  F  P  S  A  H  S  A  P  P  -109
CCCATCCTGCAGCGCCGACTTCCTGCACCTGGGGGATCTGCCAGGAGAGCCCAGCAAGAT - 480
 P  S  C  S  A  D  F  L  H  L  G  D  L  P  G  E  P  S  K  M  -129
GACAGCCTCGTCCAGCAACCCAGACCTGCTGGGAGGATGGGCTGCCTGGACCGAGACTGC - 540
 T  A  S  S  S  N  P  D  L  L  G  G  W  A  A  W  T  E  T  A  -149
AGCGTCGGCAGTGGCCCCCACGCCAGCCACAGAAGGCCCCCTCTTCTCTCCTGGAGGTCA - 600
 A  S  A  V  A  P  T  P  A  T  E  G  P  L  F  S  P  G  G  Q  -169
GCCGGCCCCTTGTGGCTCTCAGGCCAGCTGGACCAAGTCTCAGAACCCGGACCCATTTGC - 660
 P  A  P  C  G  S  Q  A  S  W  T  K  S  Q  N  P  D  P  F  A  -189
TGACCTTGGCGACCTCAGCTCCGGCCTCCAAGGCTCACCAGCTGGATTTCCTCCTGGGGG - 720
 D  L  G  D  L  S  S  G  L  Q  G  S  P  A  G  F  P  P  G  G  -209
```

FIG. 2B

```
CTTCATTCCCAAAACGGCCACCACGGCCAAAGGCAGCAGCTCCTGGCAGACAAGTCGGCC - 780
 F  I  P  K  T  A  T  T  A  K  G  S  S  S  W  Q  T  S  R  P   -229
GCCAGCCCAGGGCGCCTCATGGCCCCCTCAGGCCAAGCCGCCCCCCAAAGCCTGCACACA - 840
 P  A  Q  G  A  S  W  P  P  Q  A  K  P  P  P  K  A  C  T  Q   -249
GCCAAGGCCTAACTATGCCTCGAACTTCAGTGTGATCGGGGCGCGGGAGGAGCGGGGGGT - 900
 P  R  P  N  Y  A  S  N  F  S  V  I  G  A  R  E  E  R  G  V   -269
CCGCGCACCCAGCTTTGCTCAAAAGCCAAAAGTCTCTGAGAACGACTTTGAAGATCTGTT - 960
 R  A  P  S  F  A  Q  K  P  K  V  S  E  N  D  F  E  D  L  L   -289
GTCCAATCAAGGCTTCTCCTCCAGGTCTGACAAGAAAGGGCCAAAGACCATTGCAGAGAT - 1020
 S  N  Q  G  F  S  S  R  S  D  K  K  G  P  K  T  I  A  E  M   -309
GAGGAAGCAGGACCTGGCTAAAGACACGGACCCACTCAAGCTGAAGCTCCTGGACTGGAT - 1080
 R  K  Q  D  L  A  K  D  T  D  P  L  K  L  K  L  L  D  W  I   -329
TGAGGGCAAGGAGCGGAACATCCGGGCCCTGCTGTCCACGCTGCACACAGTGCTGTGGGA - 1140
 E  G  K  E  R  N  I  R  A  L  L  S  T  L  H  T  V  L  W  D   -349
CGGGGAGAGCCGCTGGACGCCCGTGGGCATGGCCGACCTGGTGGCTCCGGAGCAAGTGAA - 1200
 G  E  S  R  W  T  P  V  G  M  A  D  L  V  A  P  E  Q  V  K   -369
GAAGCACTATCGCCGCGCGGTGCTGGCCGTGCACCCCGACAAGGCTGCGGGGCAGCCGTA - 1260
 K  H  Y  R  R  A  V  L  A  V  H  P  D  K  A  A  G  Q  P  Y   -389
CGAGCAGCACGCCAAGATGATCTTCATGGAGCTGAATGACGCCTGGTCGGAGTTTGAGAA - 1320
 E  Q  H  A  K  M  I  F  M  E  L  N  D  A  W  S  E  F  E  N   -409
CCAGGGCTCCCGGCCCCTCTTCTGAGGCCGCAGTGGTGGTGGCTGCGCACACAGCTCCAC - 1380
 Q  G  S  R  P  L  F  *                                       - 416
```

FIG. 2C

```
AGGTTGGGAGCCGTCGTGGGACCTGGGTCCCCACCGTGAGGACCCCGTGGGCGACAGCAG - 1440
GTGTGGCCAGGGTGGGCTCCGAGCCCCGGGTCACCGCCCGCCCAGCGTTCCAGGCACAT - 1500
GAAGAGAAAGCATTCCAAAGCCTCTGATTGTTGTTTCCTTTTTCTCCTCCCGAAGGAACA - 1560
GCTGATTCATGCTCCTCCCGCAATTGTCACGTCTGTGATTTATTTGGTGTTTCGGGCGTG - 1620
GCCTCTGGAGCCCCGGCACGTGGTGGGCCACGCTGCTGGCGCTCATGGGCCCTGGTGTTT - 1680
GCACCGCACTTTGTAATCAGTCCCGTGGTTGTCTGTACAGAATTAAACTATTTTCCGATG - 1740
```

FIG. 3A

```
      1                                                          60
GAK2  ATGTCGCTGCTGCAGTCTGCGCTCGACTTCTTGGCGGGTCCAGGCTCCCTGGGCGGTGCT
GAK1  ATGTCGCTGCTGCAGTCTGCGCTCGACTTCTTGGCGGGTCCAGGCTCCCTGGGCGGTGCT
GAK   ATGTCGCTGCTGCAGTCTGCGCTCGACTTCTTGGCGGGTCCAGGCTCCCTGGGCGGTGCT

      61                                                        120
GAK2  TCCGGCCGCGACCAGAGTGACTTCGTGGGCAGACGGTGGAACTGGGCGAGCTGCGGCTG
GAK1  TCCGGCCGCGACCAGAGTGACTTCGTGGGCAGACGGTGGAACTGGGCGAGCTGCGGCTG
GAK   TCCGGCCGCGACCAGAGTGACTTCGTGGGCAGACGGTGGAACTGGGCGAGCTGCGGCTG

      121                                                       180
GAK2  C-----------------------------------------------------------
GAK1  CGGGTGCGGCGGGTCCTGGCCGAAGGAGGGTTTGCATTTGTGTATGAAGCTCAAGATGTG
GAK   CGGGTGCGGCGGGTCCTGGCCGAAGGAGGGTTTGCATTTGTGTATGAAGCTCAAGATGTG

      181                                                       240
GAK2  ------------------------------------------------------------
GAK1  GGGAGTGGCAGAGAGTATGCATTAAAGAGGCTATTATCCAATGAAGAGGAAAAGAACAGA
GAK   GGGAGTGGCAGAGAGTATGCATTAAAGAGGCTATTATCCAATGAAGAGGAAAAGAACAGA
```

FIG. 3 B

```
      241                                                        300
GAK2  ------------------------------------------------------------
GAK1  GCCATCATTCAAGAAGTTTGCTTCATGAAAAAGCTTTCCGGCCACCCGAACATTGTCCAG
GAK   GCCATCATTCAAGAAGTTTGCTTCATGAAAAAGCTTTCCGGCCACCCGAACATTGTCCAG

      301                                                        360
GAK2  ------------------------------------------------------------
GAK1  TTTTGTTCTGCAGCGTCTATAGGAAAAGAGGAGTCAGACACGGGGCAGGCTGAGTTCCTC
GAK   TTTTGTTCTGCAGCGTCTATAGGAAAAGAGGAGTCAGACACGGGGCAGGCTGAGTTCCTC

      361                                                        420
GAK2  ------------------------------------------------------------
GAK1  TTGCTCACAGAGCTCTGTAAAGGGCAGCTGGTGGAATTTTTGAAGAAAATGGAATCTCGA
GAK   TTGCTCACAGAGCTCTGTAAAGGGCAGCTGGTGGAATTTTTGAAGAAAATGGAATCTCGA

      421                                                        480
GAK2  ------------------------------------------------------------
GAK1  GGCCCCCTTTCGTGCGACACGGTTCTGAAGATCTTCTACCAGACGTGCCGCGCCGTGCAG
GAK   GGCCCCCTTTCGTGCGACACGGTTCTGAAGATCTTCTACCAGACGTGCCGCGCCGTGCAG

      481                                                        540
GAK2  ------------------------------------------------------------
GAK1  CACATGCACCGGCAGAAGCCGCCCATCATCCACAGGGACCTCAAGGTTGAGAACTTGTTG
GAK   CACATGCACCGGCAGAAGCCGCCCATCATCCACAGGGACCTCAAGGTTGAGAACTTGTTG
```

FIG. 3C

```
      541                                                        600
GAK2  ------------------------------------------------------------
GAK1  CTTAGTAACCAAGGGACCATTAAGCTGTGTGACTTTGGCAGTGCCACGACCATCTCGCAC
GAK   CTTAGTAACCAAGGGACCATTAAGCTGTGTGACTTTGGCAGTGCCACGACCATCTCGCAC

      601                                                        660
GAK2  ------------------------------------------------------------
GAK1  TACCCTGACTACAGCTGGAGCGCCCAGAGGCGAGCCCTGGTGGAGGAAGAGATCACGAGG
GAK   TACCCTGACTACAGCTGGAGCGCCCAGAGGCGAGCCCTGGTGGAGGAAGAGATCACGAGG

      661                                                        720
GAK2  ------------------------------------------------------------
GAK1  AATACAACACCAATGTATAGAACACCAGAAATCATAGACTTGTATTCCAACTTCCCGATC
GAK   AATACAACACCAATGTATAGAACACCAGAAATCATAGACTTGTATTCCAACTTCCCGATC

      721                                                        780
GAK2  ------------------------------------------------------------
GAK1  GGCGAGAAGCAGGATATCTGGGCCCTGGGCTGCATCTTGTACCTGCTGTGCTTCCGGCAG
GAK   GGCGAGAAGCAGGATATCTGGGCCCTGGGCTGCATCTTGTACCTGCTGTGCTTCCGGCAG

      781                                                        840
GAK2  ------------------------------------------------------------
GAK1  CACCCTTTTGAGGATGGAGCGAAACTTCGAATAGTCAATGGGAAGTACTCGATCCCCCCG
GAK   CACCCTTTTGAGGATGGAGCGAAACTTCGAATAGTCAATGGGAAGTACTCGATCCCCCCG
```

FIG. 3D

```
     841                                                         900
GAK2 ------------------------------------------------------------
GAK1 CACGACACGCAGTACACGGTCTTCCACAGCCTCATCCGCGCCATGCTGCAGGTGAACCCG
GAK  CACGACACGCAGTACACGGTCTTCCACAGCCTCATCCGCGCCATGCTGCAGGTGAACCCG

     901                                                         960
GAK2 ------------------------------------------------------------
GAK1 GAGGAGCGGCTGTCCATCGCCGAGGTGGTGCACCAGCTGCAGGAGATCGCGGCCGCCCGC
GAK  GAGGAGCGGCTGTCCATCGCCGAGGTGGTGCACCAGCTGCAGGAGATCGCGGCCGCCCGC

     961                                                        1020
GAK2 ------------------------------------------------------------
GAK1 AACGTGAACCCCAAGTCTCCCATCACAGAGCTCCTGGAGCAGAATGGAGGCTACGGGAGC
GAK  AACGTGAACCCCAAGTCTCCCATCACAGAGCTCCTGGAGCAGAATGGAGGCTACGGGAGC

     1021                                                       1080
GAK2 ------------------------------------------------------------
GAK1 GCCACACTGTCCCGAGGGCCACCCCCTCCCGTGGGCCCCGCTGGCAGTGGCTACAGTGGA
GAK  GCCACACTGTCCCGAGGGCCACCCCCTCCCGTGGGCCCCGCTGGCAGTGGCTACAGTGGA

     1081                                                       1140
GAK2 ------------------------------------------------------------
GAK1 GGCCTGGCGCTGGCGGAGTACGACCAGCCGTATGGCGGCTTCCTGGACATTCTGCGGGGT
GAK  GGCCTGGCGCTGGCGGAGTACGACCAGCCGTATGGCGGCTTCCTGGACATTCTGCGGGGT
```

FIG. 3E

```
      1141                                                      1200
GAK2  ------------------------------------------------------------
GAK1  GGGACAGAGCGGCTCTTCACCAACCTCAAGGACACCTCCTCCAAGGTCATCCAGTCCGTC
GAK   GGGACAGAGCGGCTCTTCACCAACCTCAAGGACACCTCCTCCAAGGTCATCCAGTCCGTC
      1201                                                      1260
GAK2  ------------------------------------------------------------
GAK1  GCTAATTATGCAAAGGGTGACCTGGACATATCTTACATCACATCCAGAATTGCAGTGATG
GAK   GCTAATTATGCAAAGGGTGACCTGGACATATCTTACATCACATCCAGAATTGCAGTGATG

      1261                                                      1320
GAK2  ------------------------------------------------------------
GAK1  TCATTCCCAGCAGAAGGTGTGGAGTCAGCGCTCAAAAACAACATCGAAGATGTGCGGTTG
GAK   TCATTCCCAGCAGAAGGTGTGGAGTCAGCGCTCAAAAACAACATCGAAGATGTGCGGTTG

      1321                                                      1380
GAK2  ------------------------------------------------------------
GAK1  TTCCTGGACTCCAAGCACCCAGGGCACTATGCCGTCTACAACCTGTCCCCGAGGACCTAC
GAK   TTCCTGGACTCCAAGCACCCAGGGCACTATGCCGTCTACAACCTGTCCCCGAGGACCTAC

      1381                                                      1440
GAK2  ------------------------------------------------------------
GAK1  CGGCCCTCCAGGTTCCACAACCGGGTCTCCGAGTGTGGCTGGGCAGCACGGCGGGCCCCA
GAK   CGGCCCTCCAGGTTCCACAACCGGGTCTCCGAGTGTGGCTGGGCAGCACGGCGGGCCCCA
```

FIG. 3F

```
     1441                                                        1500
GAK2 ------------------------------------------------------------
GAK1 CACCTGCACACCCTGTACAACATCTGCAGGAACATGCACGCCTGGCTGCGGCAGGACCAC
GAK  CACCTGCACACCCTGTACAACATCTGCAGGAACATGCACGCCTGGCTGCGGCAGGACCAC
     1501                                                        1560
GAK2 ------------------------------------------------------------
GAK1 AAGAACGTCTGCGTCGTGCACTGCATGGACGGGAGAGCCGCGTCTGCTGTGGCCGTCTGC
GAK  AAGAACGTCTGCGTCGTGCACTGCATGGACGGGAGAGCCGCGTCTGCTGTGGCCGTCTGC

     1561                                                        1620
GAK2 ------------------------------------------------------------
GAK1 TCCTTCCTGTGCTTCTGCCGTCTCTTCAGCACCGCGGAGGCCGCCGTGTACATGTTCAGC
GAK  TCCTTCCTGTGCTTCTGCCGTCTCTTCAGCACCGCGGAGGCCGCCGTGTACATGTTCAGC

     1621                                                        1680
GAK2 ------------------------------------------------------------
GAK1 ATGAAGCGCTGCCCACCAGGCATCTGGCCATCCCACAAAAGGTACATCGAGTACATGTGT
GAK  ATGAAGCGCTGCCCACCAGGCATCTGGCCATCCCACAAAAGGTACATCGAGTACATGTGT

     1681                                                        1740
GAK2 ------------------------------------------------------------
GAK1 GACATGGTGGCGGAGGAGCCCATCACACCCCACAGCAAGCCCATCCTGGTGAGGGCCGTG
GAK  GACATGGTGGCGGAGGAGCCCATCACACCCCACAGCAAGCCCATCCTGGTGAGGGCCGTG
```

FIG. 3G

```
      1741                                                      1800
GAK2  ------------------------------------------------------------
GAK1  GTCATGACACCCGTGCCGCTGTTCAGCAAGCAGAGGAGCGGCTGCAGGCCCTTCTGCGAG
GAK   GTCATGACACCCGTGCCGCTGTTCAGCAAGCAGAGGAGCGGCTGCAGGCCCTTCTGCGAG

      1801                                                      1860
GAK2  ------------------------------------------------------------
GAK1  GTCTACGTGGGGGACGAGCGTGTGGCCAGCACCTCCCAGGAGTACGACAAGATGCGGGAC
GAK   GTCTACGTGGGGGACGAGCGTGTGGCCAGCACCTCCCAGGAGTACGACAAGATGCGGGAC

      1861                                                      1920
GAK2  ------------------------------------------------------------
GAK1  TTTAAGATTGAAGATGGCAAAGCGGTGATTCCCCTGGGCGTCACGGTGCAAGGAGACGTG
GAK   TTTAAGATTGAAGATGGCAAAGCGGTGATTCCCCTGGGCGTCACGGTGCAAGGAGACGTG

      1921                                                      1980
GAK2  ------------------------------------------------------------
GAK1  CTCATCGTCATCTATCACGCCCGGTCCACTCTGGGCGGCCGGCTGCAGGCCAAGATGGCA
GAK   CTCATCGTCATCTATCACGCCCGGTCCACTCTGGGCGGCCGGCTGCAGGCCAAGATGGCA

      1981                                                      2040
GAK2  ------------------------------------------------------------
GAK1  TCCATGAAGATGTTCCAGATTCAGTTCCACACGGGGTTTGTGCCTCGGAACGCCACCACT
GAK   TCCATGAAGATGTTCCAGATTCAGTTCCACACGGGGTTTGTGCCTCGGAACGCCACCACT
```

FIG. 3H

```
      2041                                                       2100
GAK2  ------------------------------------------------------------
GAK1  GTGAAATTTGCCAAGTATGACCTGGACGCGTGTGACATTCAAGAAAAATACCCGGATTTA
GAK   GTGAAATTTGCCAAGTATGACCTGGACGCGTGTGACATTCAAGAAAAATACCCGGATTTA

      2101                                                       2160
GAK2  ------------------------------------------------------------
GAK1  TTTCAAGTGAACCTGGAAGTGGAGGTGGAGCCCAGGGACAGGCCGAGCCGGGAAGCCCCA
GAK   TTTCAAGTGAACCTGGAAGTGGAGGTGGAGCCCAGGGACAGGCCGAGCCGGGAAGCCCCA

      2161                                                       2220
GAK2  ------------------------------------------------------------
GAK1  CCATGGGAGAACTCGAGCATGAGGGGGCTGAACCCCAAAATCCTGTTTTCCAGCCGGGAG
GAK   CCATGGGAGAACTCGAGCATGAGGGGGCTGAACCCCAAAATCCTGTTTTCCAGCCGGGAG

      2221                                                       2280
GAK2  ------------------------------------------------------------
GAK1  GAGCAGCAAGACATTCTGTCTAAGTTTGGGAAGCCGGAGCTTCCCCGGCAGCCTGGCTCC
GAK   GAGCAGCAAGACATTCTGTCTAAGTTTGGGAAGCCGGAGCTTCCCCGGCAGCCTGGCTCC

      2281                                                       2340
GAK2  ------------------------------------------------------------
GAK1  ACGGCTCAGTATGATGCTGGGGCAGGGTCCCCGGAAGCCGAACCCACAGACTCTGACTCA
GAK   ACGGCTCAGTATGATGCTGGGGCAGGGTCCCCGGAAGCCGAACCCACAGACTCTGACTCA
```

FIG. 3I

```
       2341                                                        2400
GAK2   ------------------------------------------------------------
GAK1   CCGCCAAGCAGCAGCGCGGACGCCAGTCGCTTCCTGCACACGCTGGACTGGCAGGAAGAG
GAK    CCGCCAAGCAGCAGCGCGGACGCCAGTCGCTTCCTGCACACGCTGGACTGGCAGGAAGAG

       2401                                                        2460
GAK2   ------------------------------------------------------------
GAK1   AAGGAGGCAGAGACTGGTGCAGAAAATGCCTCTTCCAAGGAGAGCGAGTCTGCCCTGATG
GAK    AAGGAGGCAGAGACTGGTGCAGAAAATGCCTCTTCCAAGGAGAGCGAGTCTGCCCTGATG

       2461                                                        2520
GAK2   ------------------------------------------------------------
GAK1   GAGGACAGAGACGAGAGTGAGGTGTCAGATGAAGGGGGATCCCCGATCTCCAGCGAGGGC
GAK    GAGGACAGAGACGAGAGTGAGGTGTCAGATGAAGGGGGATCCCCGATCTCCAGCGAGGGC

       2521                                                        2580
GAK2   ------------------------------------------------------------
GAK1   CAGGAACCCAGGGCCGACCCAGAGCCCCCCGGCCTGGCAGCAGGGCTGGTGCAGCAGGAC
GAK    CAGGAACCCAGGGCCGACCCAGAGCCCCCCGGCCTGGCAGCAGGGCTGGTGCAGCAGGAC

       2581                                                        2640
GAK2   ------------------------------------------------------------
GAK1   TTGGTTTTTGAGGTGGAGACACCGGCTGTGCTGCCAGAGCCTGTGCCACAGGAAGACGGG
GAK    TTGGTTTTTGAGGTGGAGACACCGGCTGTGCTGCCAGAGCCTGTGCCACAGGAAGACGGG
```

FIG. 3J

```
      2641                                                       2700
GAK2  ------------------------------------------------------------
GAK1  GTCGACCTCCTGGGCCTGCACTCCGAGGTGGGCGCAGGGCCAGCTGTACCCCCGCAGGCC
GAK   GTCGACCTCCTGGGCCTGCACTCCGAGGTGGGCGCAGGGCCAGCTGTACCCCCGCAGGCC

      2701                                                       2760
GAK2  ------------------------------------------------------------
GAK1  TGCAAGGCCCCCTCCAGCAACACCGACCTGCTCAGCTGCCTCCTTGGCCCCCTGAGGCC
GAK   TGCAAGGCCCCCTCCAGCAACACCGACCTGCTCAGCTGCCTCCTTGGCCCCCTGAGGCC

      2761                                                       2820
GAK2  ----------------------------------------------TCCTGGCAAGCCCG
GAK1  GCCTCCCAGGGGCCCCCGGAGGATCTGCTCAGCGAGGACCCGCTGCTCCTGGCAAGCCCG
GAK   GCCTCCCAGGGGCCCCCGGAGGATCTGCTCAGCGAGGACCCGCTGCTCCTGGCAAGCCCG

      2821                                                       2880
GAK2  GCCCCTCCCCTGAGCGTGCAGAGCACCCCAAGAGGAGGCCCCCTGCCGCTGCTGACCCC
GAK1  GCCCCTCCCCTGAGCGTGCAGAGCACCCCAAGAGGAGGCCCCCTGCCGCTG---------
GAK   GCCCCTCCCCTGAGCGTGCAGAGCACCCCAAGAGGAGGCCCCCTGCCGCTGCTGACCCC

      2881                                                       2940
GAK2  TTTGGCCCGCTTCTGCCGTCTTCAGGCAACAACTCCCAGCCCTGCTCCAATCCTGATCTC
GAK1  -------------------------GCAACAACTCCCAGCCCTGCTCCAATCCTGATCTC
GAK   TTTGGCCCGCTTCTGCCGTCTTCAGGCAACAACTCCCAGCCCTGCTCCAATCCTGATCTC
```

FIG. 3K

```
     2941                                                        3000
GAK2 TTCGGCGAATTTCTCAATTCGGACTCTGTGACCGTCCCACCATCCTTCCCGTCTGCCCAC
GAK1 TTCGGCGAATTTCTCAATTCGGACTCTGTGACCGTCCCACCATCCTTCCCGTCTGCCCAC
GAK  TTCGGCGAATTTCTCAATTCGGACTCTGTGACCGTCCCACCATCCTTCCCGTCTGCCCAC

     3001                                                        3060
GAK2 AGCGCTCCGCCCCCATCCTGCAGCGCCGACTTCCTGCACCTGGGGATCTGCCAGGAGAG
GAK1 AGCGCTCCGCCCCCATCCTGCAGCGCCGACTTCCTGCACCTGGGGATCTGCCAGGAGAG
GAK  AGCGCTCCGCCCCCATCCTGCAGCGCCGACTTCCTGCACCTGGGGATCTGCCAGGAGAG

     3061                                                        3120
GAK2 CCCAGCAAGATGACAGCCTCGTCCAGCAACCCAGACCTGCTGGAGGATGGGCTGCCTGG
GAK1 CCCAGCAAGATGACAGCCTCGTCCAGCAACCCAGACCTGCTGGAGGATGGGCTGCCTGG
GAK  CCCAGCAAGATGACAGCCTCGTCCAGCAACCCAGACCTGCTGGAGGATGGGCTGCCTGG

     3121                                                        3180
GAK2 ACCGAGACTGCAGCGTCGGCAGTGGCCCCCACGCCAGCCACAGAAGGCCCCCTCTTCTCT
GAK1 ACCGAGACTGCAGCGTCGGCAGTGGCCCCCACGCCAGCCACAGAAGGCCCCCTCTTCTCT
GAK  ACCGAGACTGCAGCGTCGGCAGTGGCCCCCACGCCAGCCACAGAAGGCCCCCTCTTCTCT

     3181                                                        3240
GAK2 CCTGGAGGTCAGCCGGCCCCTTGTGGCTCTCAGGCCAGCTGGACCAAGTCTCAGAACCCG
GAK1 CCTGGAGGTCAGCCGGCCCCTTGTGGCTCTCAGGCCAGCTGGACCAAGTCTCAGAACCCG
GAK  CCTGGAGGTCAGCCGGCCCCTTGTGGCTCTCAGGCCAGCTGGACCAAGTCTCAGAACCCG
```

FIG. 3L

```
      3241                                                       3300
GAK2  GACCCATTTGCTGACCTTGGCGACCTCAGCTCCGGCCTCCAAGGCTCACCAGCTGGATTT
GAK1  GACCCATTTGCTGACCTTGGCGACCTCAGCTCCGGCCTCCAAGGCTCACCAGCTGGATTT
GAK   GACCCATTTGCTGACCTTGGCGACCTCAGCTCCGGCCTCCAAGGCTCACCAGCTGGATTT

      3301                                                       3360
GAK2  CCTCCTGGGGGCTTCATTCCCAAAACGGCCACCACGGCCAAAGGCAGCAGCTCCTGGCAG
GAK1  CCTCCTGGGGGCTTCATTCCCAAAACGGCCACCACGGCCAAAGGCAGCAGCTCCTGGCAG
GAK   CCTCCTGGGGGCTTCATTCCCAAAACGGCCACCACGGCCAAAGGCAGCAGCTCCTGGCAG

      3361                                                       3420
GAK2  ACAAGTCGGCCGCCAGCCCAGGGCGCCTCATGGCCCCCTCAGGCCAAGCCGCCCCCCAAA
GAK1  ACAAGTCGGCCGCCAGCCCAGGGCGCCTCATGGCCCCCTCAGGCCAAGCCGCCCCCCAAA
GAK   ACAAGTCGGCCGCCAGCCCAGGGCGCCTCATGGCCCCCTCAGGCCAAGCCGCCCCCCAAA

      3421                                                       3480
GAK2  GCCTGCACACAGCCAAGGCCTAACTATGCCTCGAACTTCAGTGTGATCGGGGCGCGGGAG
GAK1  GCCTGCACACAGCCAAGGCCTAACTATGCCTCGAACTTCAGTGTGATCGGGGCGCGGGAG
GAK   GCCTGCACACAGCCAAGGCCTAACTATGCCTCGAACTTCAGTGTGATCGGGGCGCGGGAG

      3481                                                       3540
GAK2  GAGCGGGGGGTCCGCGCACCCAGCTTTGCTCAAAAGCCAAAAGTCTCTGAGAACGACTTT
GAK1  GAGCGGGGGGTCCGCGCACCCAGCTTTGCTCAAAAGCCAAAAGTCTCTGAGAACGACTTT
GAK   GAGCGGGGGGTCCGCGCACCCAGCTTTGCTCAAAAGCCAAAAGTCTCTGAGAACGACTTT
```

FIG. 3M

```
      3541                                                      3600
GAK2  GAAGATCTGTTGTCCAATCAAGGCTTCTCCTCCAGGTCTGACAAGAAAGGGCCAAAGACC
GAK1  GAAGATCTGTTGTCCAATCAAGGCTTCTCCTCCAGGTCTGACAAGAAAGGGCCAAAGACC
GAK   GAAGATCTGTTGTCCAATCAAGGCTTCTCCTCCAGGTCTGACAAGAAAGGGCCAAAGACC

      3601                                                      3660
GAK2  ATTGCAGAGATGAGGAAGCAGGACCTGGCTAAAGACACGGACCCACTCAAGCTGAAGCTC
GAK1  ATTGCAGAGATGAGGAAGCAGGACCTGGCTAAAGACACGGACCCACTCAAGCTGAAGCTC
GAK   ATTGCAGAGATGAGGAAGCAGGACCTGGCTAAAGACACGGACCCACTCAAGCTGAAGCTC

      3661                                                      3720
GAK2  CTGGACTGGATTGAGGGCAAGGAGCGGAACATCCGGGCCCTGCTGTCCACGCTGCACACA
GAK1  CTGGACTGGATTGAGGGCAAGGAGCGGAACATCCGGGCCCTGCTGTCCACGCTGCACACA
GAK   CTGGACTGGATTGAGGGCAAGGAGCGGAACATCCGGGCCCTGCTGTCCACGCTGCACACA

      3721                                                      3780
GAK2  GTGCTGTGGGACGGGGAGAGCCGCTGGACGCCCGTGGGCATGGCCGACCTGGTGGCTCCG
GAK1  GTGCTGTGGGACGGGGAGAGCCGCTGGACGCCCGTGGGCATGGCCGACCTGGTGGCTCCG
GAK   GTGCTGTGGGACGGGGAGAGCCGCTGGACGCCCGTGGGCATGGCCGACCTGGTGGCTCCG

      3781                                                      3840
GAK2  GAGCAAGTGAAGAAGCACTATCGCCGCGCGGTGCTGGCCGTGCACCCCGACAAGGCTGCG
GAK1  GAGCAAGTGAAGAAGCACTATCGCCGCGCGGTGCTGGCCGTGCACCCCGACAAGGCTGCG
GAK   GAGCAAGTGAAGAAGCACTATCGCCGCGCGGTGCTGGCCGTGCACCCCGACAAGGCTGCG
```

FIG. 3N

```
     3841                                                      3900
GAK2 GGGCAGCCGTACGAGCAGCACGCCAAGATGATCTTCATGGAGCTGAATGACGCCTGGTCG
GAK1 GGGCAGCCGTACGAGCAGCACGCCAAGATGATCTTCATGGAGCTGAATGACGCCTGGTCG
GAK  GGGCAGCCGTACGAGCAGCACGCCAAGATGATCTTCATGGAGCTGAATGACGCCTGGTCG

     3901                                                      3960
GAK2 GAGTTTGAGAACCAGGGCTCCCGGCCCCTCTTCTGAGGCCGCAGTGGTGGTGGCTGCGCA
GAK1 GAGTTTGAGAACCAGGGCTCCCGGCCCCTCTTCTGAGGCCGCAGTGGTGGTGGCTGCGCA
GAK  GAGTTTGAGAACCAGGGCTCCCGGCCCCTCTTCTGAGGCCGCAGTGGTGGTGGCTGCGCA

     3961                                                      4020
GAK2 CACAGCTCCACAGGTTGGGAGCCGTCGTGGGACCTGGGTCCCCACCGTGAGGACCCCGTG
GAK1 CACAGCTCCACAGGTTGGGAGCCGTCGTGGGACCTGGGTCCCCACCGTGAGGACCCCGTG
GAK  CACAGCTCCACAGGTTGGGAGCCGTCGTGGGACCTGGGTCCCCACCGTGAGGACCCCGTG

     4021                                                      4080
GAK2 GGCGACAGCAGGTGTGGCCAGGGTGGGGCTCCGAGCCCCGGGTCACCGCCCGCCCAGCGT
GAK1 GGCGACAGCAGGTGTGGCCAGGGTGGGGCTCCGAGCCCCGGGTCACCGCCCGCCCAGCGT
GAK  GGCGACAGCAGGTGTGGCCAGGGTGGGGCTCCGAGCCCCGGGTCACCGCCCGCCCAGCGT

     4081                                                      4140
GAK2 TCCAGGCACATGAAGAGAAAGCATTCCAAAGCCTCTGATTGTTGTTTCCTTTTTCTCCTC
GAK1 TCCAGGCACATGAAGAGAAAGCATTCCAAAGCCTCTGATTGTTGTTTCCTTTTTCTCCTC
GAK  TCCAGGCACATGAAGAGAAAGCATTCCAAAGCCTCTGATTGTTGTTTCCTTTTTCTCCTC
```

FIG. 3O

```
     4141                                                        4200
GAK2 CCGAAGGAACAGCTGATTCATGCTCCTCCCGCAATTGTCACGTCTGTGATTTATTTGGTG
GAK1 CCGAAGGAACAGCTGATTCATGCTCCTCCCGCAATTGTCACGTCTGTGATTTATTTGGTG
GAK  CCGAAGGAACAGCTGATTCATGCTCCTCCCGCAATTGTCACGTCTGTGATTTATTTGGTG

     4201                                                        4260
GAK2 TTTCGGGCGTGGCCTCTGGAGCCCCGGCACGTGGTGGGCCACGCTGCTGGCGCTCATGGG
GAK1 TTTCGGGCGTGGCCTCTGGAGCCCCGGCACGTGGTGGGCCACGCTGCTGGCGCTCATGGG
GAK  TTTCGGGCGTGGCCTCTGGAGCCCCGGCACGTGGTGGGCCACGCTGCTGGCGCTCATGGG

     4261                                                        4320
GAK2 CCCTGGTGTTTGCACCGCACTTTGTAATCAGTCCCGTGGTTGTCTGTACAGAATTAAACT
GAK1 CCCTGGTGTTTGCACCGCACTTTGTAATCAGTCCCGTGGTTGTCTGTACAGAATTAAACT
GAK  CCCTGGTGTTTGCACCGCACTTTGTAATCAGTCCCGTGGTTGTCTGTACAGAATTAAACT

     4321
GAK2 ATTTTCCGATG   1646
GAK1 ATTTTCCGATG   4298
GAK  ATTTTCCGATG   4331
```

FIG. 4A

```
     1                                                          60
GAK2 MSLLQSALDFLAGPGSLGGASGRDQSDFVGQTVELGELRL--------------------
GAK1 MSLLQSALDFLAGPGSLGGASGRDQSDFVGQTVELGELRLVRRVLAEGGFAFVYEAQDV
GAK  MSLLQSALDFLAGPGSLGGASGRDQSDFVGQTVELGELRLVRRVLAEGGFAFVYEAQDV

     61                                                        120
GAK2 ------------------------------------------------------------
GAK1 GSGREYALKRLLSNEEEKNRAIIQEVCFMKKLSGHPNIVQFCSAASIGKEESDTGQAEFL
GAK  GSGREYALKRLLSNEEEKNRAIIQEVCFMKKLSGHPNIVQFCSAASIGKEESDTGQAEFL

     121                                                       180
GAK2 ------------------------------------------------------------
GAK1 LLTELCKGQLVEFLKKMESRGPLSCDTVLKIFYQTCRAVQHMHRQKPPIIHRDLKVENLL
GAK  LLTELCKGQLVEFLKKMESRGPLSCDTVLKIFYQTCRAVQHMHRQKPPIIHRDLKVENLL

     181                                                       240
GAK2 ------------------------------------------------------------
GAK1 LSNQGTIKLCDFGSATTISHYPDYSWSAQRRALVEEEITRNTTPMYRTPEIIDLYSNFPI
GAK  LSNQGTIKLCDFGSATTISHYPDYSWSAQRRALVEEEITRNTTPMYRTPEIIDLYSNFPI
```

FIG. 4B

```
      241                                                          300
GAK2  ------------------------------------------------------------
GAK1  GEKQDIWALGCILYLLCFRQHPFEDGAKLRIVNGKYSIPPHDTQYTVFHSLIRAMLQVNP
GAK   GEKQDIWALGCILYLLCFRQHPFEDGAKLRIVNGKYSIPPHDTQYTVFHSLIRAMLQVNP

      301                                                          360
GAK2  ------------------------------------------------------------
GAK1  EERLSIAEVVHQLQEIAAARNVNPKSPITELLEQNGGYGSATLSRGPPPPVGPAGSGYSG
GAK   EERLSIAEVVHQLQEIAAARNVNPKSPITELLEQNGGYGSATLSRGPPPPVGPAGSGYSG

      361                                                          420
GAK2  ------------------------------------------------------------
GAK1  GLALAEYDQPYGGFLDILRGGTERLFTNLKDTSSKVIQSVANYAKGDLDISYITSRIAVM
GAK   GLALAEYDQPYGGFLDILRGGTERLFTNLKDTSSKVIQSVANYAKGDLDISYITSRIAVM

      421                                                          480
GAK2  ------------------------------------------------------------
GAK1  SFPAEGVESALKNNIEDVRLFLDSKHPGHYAVYNLSPRTYRPSRFHNRVSECGWAARRAP
GAK   SFPAEGVESALKNNIEDVRLFLDSKHPGHYAVYNLSPRTYRPSRFHNRVSECGWAARRAP

      481                                                          540
GAK2  ------------------------------------------------------------
GAK1  HLHTLYNICRNMHAWLRQDHKNVCVVHCMDGRAASAVAVCSFLCFCRLFSTAEAAVYMFS
GAK   HLHTLYNICRNMHAWLRQDHKNVCVVHCMDGRAASAVAVCSFLCFCRLFSTAEAAVYMFS
```

FIG. 4C

```
     541                                                        600
GAK2 ------------------------------------------------------------
GAK1 MKRCPPGIWPSHKRYIEYMCDMVAEEPITPHSKPILVRAVVMTPVPLFSKQRSGCRPFCE
GAK  MKRCPPGIWPSHKRYIEYMCDMVAEEPITPHSKPILVRAVVMTPVPLFSKQRSGCRPFCE

     601                                                        660
GAK2 ------------------------------------------------------------
GAK1 VYVGDERVASTSQEYDKMRDFKIEDGKAVIPLGVTVQGDVLIVIYHARSTLGGRLQAKMA
GAK  VYVGDERVASTSQEYDKMRDFKIEDGKAVIPLGVTVQGDVLIVIYHARSTLGGRLQAKMA

     661                                                        720
GAK2 ------------------------------------------------------------
GAK1 SMKMFQIQFHTGFVPRNATTVKFAKYDLDACDIQEKYPDLFQVNLEVEVEPRDRPSREAP
GAK  SMKMFQIQFHTGFVPRNATTVKFAKYDLDACDIQEKYPDLFQVNLEVEVEPRDRPSREAP

     721                                                        780
GAK2 ------------------------------------------------------------
GAK1 PWENSSMRGLNPKILFSSREEQQDILSKFGKPELPRQPGSTAQYDAGAGSPEAEPTDSDS
GAK  PWENSSMRGLNPKILFSSREEQQDILSKFGKPELPRQPGSTAQYDAGAGSPEAEPTDSDS

     781                                                        840
GAK2 ------------------------------------------------------------
GAK1 PPSSSADASRFLHTLDWQEEKEAETGAENASSKESESALMEDRDESEVSDEGGSPISSEG
GAK  PPSSSADASRFLHTLDWQEEKEAETGAENASSKESESALMEDRDESEVSDEGGSPISSEG
```

FIG. 4D

```
     841                                                          900
GAK2 ------------------------------------------------------------
GAK1 QEPRADPEPPGLAAGLVQQDLVFEVETPAVLPEPVPQEDGVDLLGLHSEVGAGPAVPPQA
GAK  QEPRADPEPPGLAAGLVQQDLVFEVETPAVLPEPVPQEDGVDLLGLHSEVGAGPAVPPQA

     901                                                          960
GAK2 -----------------------------------LLASPAPPLSVQSTPRGGPPAAADP
GAK1 CKAPSSNTDLLSCLLGPPEAASQGPPEDLLSEDPLLLASPAPPLSVQSTPRGGPPAA---
GAK  CKAPSSNTDLLSCLLGPPEAASQGPPEDLLSEDPLLLASPAPPLSVQSTPRGGPPAAADP

     961                                                         1020
GAK2 FGPLLPSSGNNSQPCSNPDLFGEFLNSDSVTVPPSFPSAHSAPPPSCSADFLHLGDLPGE
GAK1 --------GNNSQPCSNPDLFGEFLNSDSVTVPPSFPSAHSAPPPSCSADFLHLGDLPGE
GAK  FGPLLPSSGNNSQPCSNPDLFGEFLNSDSVTVPPSFPSAHSAPPPSCSADFLHLGDLPGE

     1021                                                        1080
GAK2 PSKMTASSSNPDLLGGWAAWTETAASAVAPTPATEGPLFSPGGQPAPCGSQASWTKSQNP
GAK1 PSKMTASSSNPDLLGGWAAWTETAASAVAPTPATEGPLFSPGGQPAPCGSQASWTKSQNP
GAK  PSKMTASSSNPDLLGGWAAWTETAASAVAPTPATEGPLFSPGGQPAPCGSQASWTKSQNP

     1081                                                        1140
GAK2 DPFADLGDLSSGLQGSPAGFPPGGFIPKTATTAKGSSSWQTSRPPAQGASWPPQAKPPPK
GAK1 DPFADLGDLSSGLQGSPAGFPPGGFIPKTATTAKGSSSWQTSRPPAQGASWPPQAKPPPK
GAK  DPFADLGDLSSGLQGSPAGFPPGGFIPKTATTAKGSSSWQTSRPPAQGASWPPQAKPPPK
```

FIG. 4E

```
      1141                                                        1200
GAK2  ACTQPRPNYASNFSVIGAREERGVRAPSFAQKPKVSENDFEDLLSNQGFSSRSDKKGPKT
GAK1  ACTQPRPNYASNFSVIGAREERGVRAPSFAQKPKVSENDFEDLLSNQGFSSRSDKKGPKT
GAK   ACTQPRPNYASNFSVIGAREERGVRAPSFAQKPKVSENDFEDLLSNQGFSSRSDKKGPKT

      1201                                                        1260
GAK2  IAEMRKQDLAKDTDPLKLKLLDWIEGKERNIRALLSTLHTVLWDGESRWTPVGMADLVAP
GAK1  IAEMRKQDLAKDTDPLKLKLLDWIEGKERNIRALLSTLHTVLWDGESRWTPVGMADLVAP
GAK   IAEMRKQDLAKDTDPLKLKLLDWIEGKERNIRALLSTLHTVLWDGESRWTPVGMADLVAP

      1261
GAK2  EQVKKHYRRAVLAVHPDKAAGQPYEQHAKMIFMELNDAWSEFENQGSRPLF      416
GAK1  EQVKKHYRRAVLAVHPDKAAGQPYEQHAKMIFMELNDAWSEFENQGSRPLF     1300
GAK   EQVKKHYRRAVLAVHPDKAAGQPYEQHAKMIFMELNDAWSEFENQGSRPLF     1311
```

HUMAN GAK-RELATED GENE VARIANTS ASSOCIATED WITH LUNG CANCER

This is a divisional of application Ser. No. 10/102,549 (now U.S. Pat. No. 6,953,669) filed on Mar. 20, 2002 and claims the benefit thereof and incorporates the same by reference.

FIELD OF THE INVENTION

The invention relates to the nucleic acid of novel human GAK-related gene variants and the polypeptide encoded thereby, the preparation process thereof, and the uses of the same in diagnosing diseases associated with the variants, in particular, homeostasis impairment-related diseases and non-small cell lung cancer, e.g. large cell lung cancer.

BACKGROUND OF THE INVENTION

Lung cancer is one of the major causes of cancer-related deaths in the world. There are two primary types of lung cancers: small cell lung cancer (SCLC) and non-small cell lung cancer (NSCLC) (Carney, (1992a) Curr. Opin. Oncol. 4: 292–8). Small cell lung cancer accounts for approximately 25% of lung cancer and spreads aggressively (Smyth et al. (1986) Q J Med. 61: 969–76; Carney, (1992b) Lancet 339: 843–6). Non-small cell lung cancer represents the majority (about 75%) of lung cancer and is further divided into three main subtypes: squamous cell carcinoma, adenocarcinoma, and large cell carcinoma (Ihde and Minna, (1991) Cancer 15: 105–54). In recent years, much progress has been made toward understanding the molecular and cellular biology of lung cancers. Many important contributions have been made by the identification of several key genetic factors associated with lung cancers. However, the treatments of lung cancers still mainly depend on surgery, chemotherapy, and radiotherapy. This is because the molecular mechanisms underlying the pathogenesis of lung cancers remain largely unclear.

A recent hypothesis suggested that lung cancer is caused by genetic mutations of at least 10 to 20 genes (Sethi, (1997) BMJ. 314: 652–655). Therefore, future strategies for the prevention and treatment of lung cancers will be focused on the elucidation of these genetic substrates, in particular, the genes associated with the cell cycle regulation in lung cancers since it is believed that dysregulation of cell cycle may lead to the initiation and progression of cancers. Cyclins, regulators of cell cycle in eukaryotic cells (Hunter and Pines, (1991) Cell 66:1071–4), have been shown to be associated with cancers (Hunter and Pines, (1991) Cell 66:1071–4; Lammie et al. (1991) Oncogene 6:439–44; Jiang et al. (1992) Cancer Res 52:2980–3; Keyomarsi and Pardee, (1993) Proc Natl Acad Sci 90:1112–6; Weinstat-Saslow et al. (1995) Nat Med 1:1257–60). Cyclin G, a member of the cyclin family, has been shown to be associated with the carcinogenic process (Skotzko et al. (1995) Cancer Res 55:5493–8; Reimer et al. (1999) J Biol Chem 274:11022–9) mediated via p53 (a tumor suppressor gene) cell growth regulatory pathways (Okamoto and Beach, (1994) EMBO J 13:4816–22; Home et al. (1996) J Biol Chem 271:6050–61; Bates et al. (1996) Oncogene 13:1103–9; Smith et al. (1997) Exp Cell Res 230:61–8). The involvement of p53 gene in NSCLC (Kohno et al. (1999) Cancer 85: 341–7) suggests that the genes associated with cyclin G may be involved in the carcinogenesis of lung cancers. Therefore, the cyclin G-associated protein kinase (GAK), a partner of cyclin G (Kanaoka et al. (1997) FEBS Lett 402:73–80), is expected to be an important molecule for lung cancers.

The human GAK gene (Kimura et al. (1997) Genomics 44:179–87) contains an open reading frame (ORP) of 3933bp encoding 1311 amino acids. Sequence analysis demonstrated that GAK contains a Ser/Thr kinase domain, a tensin/auxilin homologous domain, and a Tyr phosphorylation target site. Using FISH technique, GAK was assigned to the chromosome 4p16 (Kimura et al. (1997) Genomics 44:179–87), a chromosomal region frequently altered in lung cancers (Michelland et al. (1999) Cancer Genet Cytogenet 114:22–30). Taken together with the discovery of gene variants of NOC2 (localized on chromosome 17p) as potential diagnostic markers for lung cancers (U.S. patent Ser. No. 09/964275), we believe that the discovery of GAK-related gene variants may also be important targets for diagnostic markers of lung cancers.

SUMMARY OF THE INVENTION

The present invention provides two GAK gene variants (GAK1 and GAK2) present in human lung tissues. The nucleotide sequences of these variants and the polypeptide sequences encoded thereby can be used for the diagnosis of diseases associated with the deficiency of GAK gene, in particular, homeostasis impairment-related diseases and non-small cell lung cancer, e.g. large cell lung cancer.

The invention further provides an expression vector and host cell for expressing the polypeptides of the invention.

The invention further provides a method for producing the polypeptides encoded by the variants of the invention.

The invention further provides an antibody specifically binding to the polypeptides.

The invention also provides methods for diagnosing diseases associated with GAK gene, in particular, homeostasis impairment-related diseases and non-small cell lung cancer, e.g. large cell lung cancer.

BRIEF DESCRIPTION OF THE DRAWINGS

FIGS. 1A–F show the nucleic acid sequence (SEQ ID NO:1) and amino acid sequence (SEQ ID NO:2) of GAK1.

FIGS. 2A–C show the nucleic acid sequence (SEQ ID NO:3) and amino acid sequence (SEQ ID NO:4) of GAK2.

FIGS. 3A–O show the nucleotide sequence alignment between the human GAK gene and its related gene variants (GAK1 and GAK2).

FIGS. 4A–E show the amino acid sequence alignment between the human GAK protein and its related gene variants (GAK1 and GAK2).

DETAILED DESCRIPTION OF THE INVENTION

According to the present invention, all technical and scientific terms used have the same meanings as commonly understood by persons skilled in the art.

The term "antibody" used herein denotes intact molecules (a polypeptide or group of polypeptides) as well as fragments thereof, such as Fab, $R(ab')_2$, and Fv fragments, which are capable of binding the epitopic determinant. Antibodies are produced by specialized B cells after stimulation by an antigen. Structurally, an antibody consists of four subunits including two heavy chains and two light chains. The internal surface shape and charge distribution of the antibody binding domain is complementary to the features of an antigen. Thus, the antibody can specifically act against the antigen in an immune response.

The term "base pair (bp)" used herein denotes nucleotides composed of a purine on one strand of DNA which can be hydrogen bonded to a pyrimidine on the other strand. Thymine (or uracil) and adenine residues are linked by two hydrogen bonds. Cytosine and guanine residues are linked by three hydrogen bonds.

The term "Basic Local Alignment Search Tool (BLAST; Altschul et al., (1997) Nucleic Acids Res. 25: 3389–3402)" used herein denotes programs for evaluation of homologies between a query sequence (amino or nucleic acid) and a test sequence as described by Altschul et al. (Nucleic Acids Res. 25: 3389–3402, 1997). Specific BLAST programs are described as follows:

(1) BLASTN compares a nucleotide query sequence with a nucleotide sequence database;

(2) BLASTP compares an amino acid query sequence with a protein sequence database;

(3) BLASTX compares the six-frame conceptual translation products of a query nucleotide sequence with a protein sequence database;

(4) TBLASTN compares a query protein sequence with a nucleotide sequence database translated in all six reading frames; and (5) TBLASTX compares the six-frame translations of a nucleotide query sequence with the six-frame translations of a nucleotide sequence database.

The term "cDNA" used herein denotes nucleic acids synthesized from a mRNA template using reverse transcriptase.

The term "cDNA library" used herein denotes a library composed of complementary DNAs which are reverse-transcribed from mRNAs.

The term "complement" used herein denotes a polynucleotide sequence capable of forming base pairing with another polynucleotide sequence. For example, the sequence 5'-ATGGACTTACT-3' binds to the complementary sequence 5'-AGTAAGTCCAT-3'.

The term "deletion" used herein denotes a removal of a portion of one or more amino acid residues/nucleotides from a gene.

The term "expressed sequence tags (ESTs)" used herein denotes short (200 to 500 base pairs) nucleotide sequences derived from either 5' or 3' end of a cDNA.

The term "expression vector" used herein denotes nucleic acid constructs which contain a cloning site for introducing the DNA into the vector, one or more selectable markers for selecting vectors containing the DNA, an origin of replication for replicating the vector whenever the host cell divides, a terminator sequence, a polyadenylation signal, and a suitable control sequence which can effectively express the DNA in a suitable host. The suitable control sequence may include promoter, enhancer and other regulatory sequences necessary for directing polymerases to transcribe the DNA.

The term "host cell" used herein denotes a cell which is used to receive, maintain, and allow the reproduction of an expression vector comprising DNA. Host cells are transformed or transfected with suitable vectors constructed using recombinant DNA methods. The recombinant DNA introduced with the vector is replicated whenever the cell divides.

The term "insertion" or "addition" used herein denotes the addition of a portion of one or more amino acid residues/nucleotides to a gene.

The term "in silico" used herein denotes a process of using computational methods (e.g., BLAST) to analyze DNA sequences.

The term "polymerase chain reaction (PCR) used herein denotes a method which increases the copy number of a nucleic acid sequence using a DNA polymerase and a set of primers (about 20bp oligonucleotides complementary to each strand of DNA) under suitable conditions (successive rounds of primer annealing, strand elongation, and dissociation).

The term "protein" or "polypeptide" used herein denotes a sequence of amino acids in a specific order that can be encoded by a gene or by a recombinant DNA. It can also be chemically synthesized.

The term "nucleic acid sequence" or "polynucleotide" used herein denotes a sequence of nucleotide (guanine, cytosine, thymine or adenine) in a specific order that can be a natural or synthesized fragment of DNA or RNA. It may be single-stranded or double-stranded.

The term "reverse transcriptase-polymerase chain reaction (RT-PCR)" used herein denotes a process which transcribes mRNA to complementary DNA strand using reverse transcriptase followed by polymerase chain reaction to amplify the specific fragment of DNA sequences.

The term "transformation" used herein denotes a process describing the uptake, incorporation, and expression of exogenous DNA by prokaryotic host cells.

The term "transfection" used herein denotes a process describing the uptake, incorporation, and expression of exogenous DNA by eukaryotic host cells.

The term "variant" used herein denotes a fragment of sequence (nucleotide or amino acid) inserted or deleted by one or more nucleotides/amino acids.

According to the present invention, the polypeptides of two novel human GAK-related gene variants and fragments thereof, and the nucleic acid sequences encoding the same are provided.

According to the present invention, the human GAK cDNA sequence was used to query the human lung EST databases (a normal lung and a large cell lung cancer) using BLAST program to search for GAK-related gene variants. Two human cDNA partial sequences (i.e., ESTs) deposited in the databases showing similarity to GAK were isolated and sequenced. These clones (named GAK1 and GAK2) were both isolated from large cell lung cancer cDNA library. FIGS. 1A–F and 2A–C show the nucleic acid sequences (SEQ ID NOs:1, and 3) of the variants and corresponding amino acid sequences (SEQ ID NOs:2, and 4) encoded thereby.

The full-length of the GAK1 cDNA is a 4308bp clone containing a 3900bp open reading frame (ORF) extending from nucleotides 11 to 3910, which corresponds to an encoded protein of 1300 amino acid residues with a predicted molecular mass of 142.1 kDa. The full-length of the GAK2 cDNA is a 1740bp clone containing a 1248bp ORF extending from nucleotides 95 to 1342, which corresponds to an encoded protein of 416 amino acid residues with a predicted molecular mass of 43.9 kDa. The sequences around the initiation ATG codon of GAK1 (located at nucleotides 11 to 13) and of GAK2 (located at nucleotides 95 to 97) were matched with the Kozak consensus sequence (A/GCCATGG) (Kozak, (1987) Nucleic Acids Res. 15: 8125–48; Kozak, (1991) J Cell Biol. 115: 887–903.). To determine the variations (insertion/deletion) in sequences of GAK1 and GAK2 cDNA clones, an alignment of GAK nucleotide/amino acid sequence with these clones was performed (FIGS. 3A–O and 4A–E). Two major genetic deletions were found in the aligned sequences. GAK1 is an in-frame 33bp (encoding 11 amino acid residues) deletion in the coding regions of GAK sequence from nucleotides 2873 to 2905. GAK2 is an in-frame 2685bp (encoding 895 amino acid residues) deletion in the coding regions of GAK sequence from nucleotides 122 to 2806.

In the present invention, a search of ESTs deposited in dbEST (Boguski et al., (1993) Nat Genet. 4: 332–3) at NCBI was performed. ESTs matched to the sequence fragments that contain genetic changes (deletion) were identified. Five ESTs were found to confirm the missing region described in GAK1 and GAK2. Four ESTs (GenBank accession number BG746688; BG333001; BG821224; BI026835), confirmed the absence of 33bp region on GAK1 nucleotide sequence, was found to be isolated from cDNA libraries derived from large cell lung cancer, colon adenocarcinoma, and marrow tissues. This suggests that the absence of 33bp fragment may serve as an important indicator for cancers. The other one EST (GenBank accession number BE619037), confirmed the absence of 2685bp region on GAK2 nucleotide sequence, was found to be isolated from a large cell lung cancer cDNA library. This suggests that the absence of the 2685bp fragment may be a useful marker for large cell lung cancer diagnosis.

Therefore, any nucleotide fragments comprising nucleotides 2870 to 2875 (encoding amino acid residues 954 to 955) of GAK1 and nucleotides 119 to 124 (encoding amino acid residue 9 to 10) of GAK2 may be used as probes for determining the presence of the variants under high stringency conditions. An alternative approach is that any set of primers for amplifying the fragment containing nucleotides 2870 to 2875 of GAK1 and nucleotides 119 to 124 of GAK2 may be used for determining the presence of the variants.

A search of the predicted protein products of GAK1 against the profile entries in PROSITE (ScanProsite) shows that GAK1 contains five N-glycosylation sites (amino acid residues 677 to 680, 724 to 727, 809 to 812, 959 to 962, and 1141 to 1144), one cAMP- and cGMP-dependent protein kinase phosphorylation site (amino acid residues 90 to 93), seventeen protein kinase C phosphorylation sites (amino acid residues 21 to 23, 62 to 64, 155 to 157, 186 to 188, 382 to 384, 393 to 395, 414 to 416, 456 to 458, 459 to 461, 540 to 542, 551 to 553, 661 to 663, 680 to 682, 726 to 728, 737 to 739, 811 to 813, and 1110 to 1112), seventeen casein kinase II phosphorylation sites (amino acid residues 6 to 9, 21 to 24, 62 to 65, 73 to 76, 305 to 308, 530 to 533, 611 to 614, 737 to 741, 776 to 779, 784 to 787, 805 to 808, 811 to 814, 906 to 909, 965 to 968, 1018 to 1021, 1165 to 1168, and 1180 to 1183), one Tyrosine kinase phosphorylation site (amino acid residues 405 to 412), seventeen N-myristoylation sites (amino acid residues 15 to 20, 18 to 23, 193 to 198, 336 to 341, 355 to 360, 361 to 366, 426 to 431, 547 to 552, 769 to 774, 806 to 811, 833 to 838, 851 to 856, 891 to 896, 952 to 957, 1024 to 1029, 1058 to 1063, and 1084 to 1089), and one Serine/Threonine protein kinases active-site signature (amino acid residues 169 to 181). Scanning a sequence against protein profile databases (ProfileScan) indicates that GAK1 protein contains a protein kinase domain (amino acid residues 40 to 314) and a proline-rich region (amino acid residues 894 to 1136). A comparison of the protein domain sequence search between GAK1 and GAK shows that GAK1 sequence is only 33bp (11aa) shorter than GAK sequence. The results indicate that the segment deleted in GAK1 sequence is located on the proline-rich region. The partial deletion of the proline-rich region observed in GAK1 suggests that the functional role of GAK1 may not be the same as GAK. However, it is believable that the presence of GAK1 may be associated with lung cancer.

A search of the predicted protein products of GAK2 against the profile entries in PROSITE (ScanProsite) shows that GAK2 protein contains two N-glycosylation sites (amino acid residues 75 to 78 and 257 to 260), six protein kinase C phosphorylation sites (amino acid residues 21 to 23, 54 to 56, 217 to 219, 226 to 228, 295 to 297, and 298 to 300), six casein kinase II phosphorylation sites (amino acid residues 6 to 9, 21 to 24, 81 to 84, 134 to 137, 281 to 284, and 296 to 299), six N-myristoylation sites (amino acid residues 15 to 20, 18 to 23, 57 to 62, 140 to 145, 174 to 179, and 200 to 205), and one TonB-dependent receptor proteins signature (amino acid residues 1 to 100). Scanning a sequence against protein profile databases (ProfileScan) indicates that GAK2 protein contains a proline-rich region (amino acid residues 45 to 252). A comparison of GAK2 and GAK in protein domain sequence search indicates that GAK2 contain a TonB-dependent receptor proteins signature being different from GAK, and suggests that this in-frame 895aa sequence deletion has made the functional role of GAK2 different from that of GAK. It should be noted that the sequence of GAK2 was found to match a complete sequence of a cDNA clone deposited in GenBank (accession number BC008668). This clone was isolated from a cDNA library prepared using lung large cell carcinoma tissue.

The presence of TonB-dependent receptor proteins signature in GAK2 suggests that GAK2 may play a role in iron regulation since the biological function of TonB-dependent receptor protein has been identified to relate to the acquisition of iron in the host cells infected by bacteria (Lundrigan and Kadner, (1986) J Biol Chem 261:10797–801; Schramm et al. (1987) J Bacteriol 169:3350–7; Ogunnariwo and Schryvers, (2001) J Bacteriol 183:890–6). Impairment of iron homeostasis has been reported to be associated with the increase of the risk of many diseases such as cancer (Weinberg (1996) Eur J Cancer Prev 5:19–36), acute myocardial infarction (Tuomainen ET AL. (1998) Circulation 97:1461–6); neural disorder (Earley et al. (2000) J Neurosci Res 62:623–8), sudden infant death (Weinberg (2001) Med Hypotheses 56:731–4; and infection (Weinberg (1992) Life Sci 50:1289–97). Therefore, the presence of GAK2 may be a useful diagnostic marker not only for lung cancers (in particular large cell lung cancer) but also for iron homeostasis impairment-related diseases.

According to the present invention, the polypeptides of the human GAK-related gene variants and the fragments thereof may be produced through genetic engineering techniques. In this case, they are produced by appropriate host cells that have been transformed by DNAs that code the polypeptides or the fragments thereof. The nucleotide sequence encoding the polypeptide of the human GAK-related gene variants or the fragments thereof is inserted into an appropriate expression vector, i.e., a vector which contains the necessary elements for the transcription and translation of the inserted coding sequence in a suitable host. The nucleic acid sequence is inserted into the vector in a manner that it will be expressed under appropriate conditions (e.g., in proper orientation and correct reading frame and with appropriate expression sequences, including an RNA polymerase binding sequence and a ribosomal binding sequence).

Any method that is known to those skilled in the art may be used to construct expression vectors containing the sequences encoding the polypeptides of the human GAK-related gene variants and appropriate transcriptional/translational control elements. These methods may include in vitro recombinant DNA and synthetic techniques, and in vivo genetic recombinants. (See, e.g., Sambrook, J. Cold Spring Harbor Press, Plainview N.Y., ch. 4, 8, and 16–17; Ausubel, R. M. et al. (1995) Current protocols in Molecular Biology, John Wiley & Sons, New York N.Y., ch. 9, 13, and 16.)

A variety of expression vector/host systems may be utilized to express the polypeptide-coding sequence. These include, but are not limited to, microorganisms such as bacteria transformed with recombinant bacteriophage, plasmid, or cosmid DNA expression vector; yeast transformed with yeast expression vector; insect cell systems infected with virus (e.g., baculovirus); plant cell system transformed with viral expression vector (e.g., cauliflower mosaic virus, CaMV, or tobacco mosaic virus, TMV); or animal cell system infected with virus (e.g., vaccina virus, adenovirus, etc.). Preferably, the host cell is a bacterium, and most preferably, the bacterium is *E. coli*.

Alternatively, the polypeptides of the GAK1 and GAK2, or the fragments thereof may be synthesized by using chemical methods. For example, peptide synthesis can be performed using various solid-phase techniques (Roberge, J. Y. et al. (1995) Science 269: 202 to 204). Automated synthesis may be achieved using the ABI 431A peptide synthesizer (Perkin-Elmer).

According to the present invention, the fragments of the polypeptides and the nucleic acid sequences of the human GAK1 and GAK2 are used as immunogens and primers or probes, respectively. It is preferable to use the purified fragments of the human GAK1 and GAK2. The fragments may be produced by enzyme digestion, chemical cleavage of isolated or purified polypeptide or nucleic acid sequences, or chemical synthesis and then may be isolated or purified. Such isolated or purified fragments of the polypeptides and nucleic acid sequences can be directly used as immunogens and primers or probes, respectively.

The present invention further provides the antibodies which specifically bind one or more out-surface epitopes of the polypeptides of the human GAK1 and GAK2.

According to the present invention, immunization of mammals with immunogens described herein, preferably humans, rabbits, rats, mice, sheep, goats, cows, or horses, is performed following procedures well known to those skilled in the art, for the purpose of obtaining antisera containing polyclonal antibodies or hybridoma lines secreting monoclonal antibodies.

Monoclonal antibodies can be prepared by standard techniques, given the teachings contained herein. Such techniques are disclosed, for example, in U.S. Pat. Nos. 4,271,145 and 4,196,265. Briefly, an animal is immunized with the immunogen. Hybridomas are prepared by fusing spleen cells from the immunized animal with myeloma cells. The fusion products are screened for those producing antibodies that bind to the immunogen. The positive hybridoma clones are isolated, and the monoclonal antibodies are recovered from those clones.

Immunization regimens for production of both polyclonal and monoclonal antibodies are well-known in the art. The immunogen may be injected by any of a number of routes, including subcutaneous, intravenous, intraperitoneal, intradermal, intramuscular, mucosal, or a combination thereof. The immunogen may be injected in soluble form, aggregate form, attached to a physical carrier, or mixed with an adjuvant, using methods and materials well-known in the art. The antisera and antibodies may be purified using column chromatography methods well known to those skilled in the art.

According to the present invention, antibody fragments which contain specific binding sites for the polypeptides or the fragments thereof may also be generated. For example, such fragments include, but are not limited to, $F(ab')_2$ fragments produced by pepsin digestion of the antibody molecule and Fab fragments generated by reducing the disulfide bridges of the $F(ab')_2$ fragments.

Many gene variants have been found to be associated with diseases (Stallings-Mann et al., (1996) Proc Natl Acad Sci USA 93: 12394–9; Liu et al., (1997) Nat Genet 16:328–9; Siffert et al., (1998) Nat Genet 18: 45 to 8; Lukas et al., (2001) Cancer Res 61: 3212 to 9). Since GAK is associated with a region (chromosome 4p) of frequent loss of heterozygosity in NSCLC, it is advisable that the gene variants of the present invention, which have genetic deletion of nucleotide/amino acid sequences, may result in cancer development and may be useful as markers for the diagnosis of human lung cancer. Based on the cDNA libraries of the matched ESTs, GAK2 can be specifically associated with large cell lung cancer whereas GAK1 can be associated with general cancers. Thus, the expression level of GAK1 or GAK2 relative to GAK may be a useful indicator for screening of patients suspected of having cancers or large cell lung cancer, respectively. This suggests that the index of relative expression level (mRNA or protein) may associate with an increased susceptibility to cancers or NSCLC, more preferably, large cell lung cancer. The fragments of GAK1 and GAK2 transcripts (mRNAs) may be detected by RT-PCR approach. Polypeptides of GAK1 and GAK2 may be determined by the binding of antibodies to these polypeptides. These approaches may be performed in accordance with conventional methods well known by persons skilled in the art.

The subject invention also provides methods for diagnosing the diseases associated with the deficiency of GAK in a mammal, in particular, homeostasis impairment-related diseases and non-small cell lung cancer, e.g. large cell lung cancer.

The method for diagnosing the diseases associated with the deficiency of GAK may be performed by detecting the nucleotide sequences of GAK1 and GAK2 variants of the invention, which comprises the steps of: (1) extracting total RNA of cells obtained from a mammal; (2) amplifying the RNA by reverse transcriptase-polymerase chain reaction (RT-PCR) with a set of primers to obtain a cDNA comprising the fragments comprising nucleotides 2870 to 2875 of SEQ ID NO: 1 or nucleotides 119 to 124 of SEQ ID NO: 3; and (3) detecting whether the cDNA sample is obtained. If necessary, the amount of the obtained cDNA sample may be detected.

In the above embodiment, one of the primers may be designed to have a sequence comprising the nucleotides 2870 to 2875 of SEQ ID NO: 1 or the nucleotides 119 to 124 of SEQ ID NO: 3, and the other may be designed to have a sequence complementary to the nucleotides of SEQ ID NO: 1 at any other locations downstream of nucleotide 2875 or to have a sequence complementary to the nucleotides of SEQ ID NO: 3 at any other locations downstream of nucleotide 124. Alternatively, one of the primers may be designed to have a sequence complementary to the nucleotides of SEQ ID NO: 1 containing nucleotides 2870 to 2875 or to have a sequence complementary to the nucleotides of SEQ ID NO: 3 containing nucleotides 119 to 124, and the other may be designed to have a sequence comprising the nucleotides of SEQ ID NO: 1 at any other locations upstream of nucleotide 2870 or to have a sequence comprising the nucleotides of SEQ ID NO: 3 at any other locations upstream of nucleotide 119. In this case, only GAK1 or GAK2 will be amplified.

Alternatively, one of the primers may be designed to have a sequence comprising the nucleotides of SEQ ID NO: 1 upstream of nucleotide 2872 or to have a sequence comprising the nucleotides of SEQ ID NO: 3 upstream of nucleotide 121, and the other may be designed to have a sequence complementary to the nucleotides of SEQ ID NO: 1 downstream of nucleotide 2873 or to have a sequence complementary to the nucleotides of SEQ ID NO: 3 downstream of nucleotide 122. Alternatively, one of the primers may be designed to have a sequence complementary to the nucleotides of SEQ ID NO: 1 upstream of nucleotide 2872 or to have a sequence complementary to the nucleotides of SEQ ID NO: 3 upstream of nucleotide 121, and the other may be designed to have a sequence comprising the nucleotides of SEQ ID NO: 1 downstream of nucleotide 2873 or to have a sequence comprising the nucleotides of SEQ ID NO: 3 downstream of nucleotide 122. In this case, GAK, GAK1 and GAK2 will be amplified. The length of the PCR fragment from GAK1 will be 33bp shorter than that from GAK, and that of the PCR fragment from GAK2 will be 2685bp shorter than that from GAK.

Preferably, the primers of the invention contain 15 to 30 nulceotides.

Total RNA may be isolated from patient samples by using TRIZOL reagents (Life Technology). Tissue samples (e.g., biopsy samples) are powdered under liquid nitrogen before homogenization. RNA purity and integrity are assessed by absorbance at 260/280 nm and by agarose gel electrophoresis. The set of primers designed to amplify the expected size of specific PCR fragments of GAK1 or GAK2 can be used. PCR fragments are analyzed on a 1% agarose gel using five microliters (10%) of the amplified products. To determine the expression levels for each gene variants, the intensity of the PCR products may be determined by using the Molecular Analyst program (version 1.4.1; Bio-Rad).

The RT-PCR experiment may be performed according to the manufacturer instructions (Boehringer Mannheim). A 50 μl reaction mixture containing 2 μl total RNA (0.1 μg/μl), 1 μl each primer (20 pM), 1 μl each dNTP (10 mM), 2.5 μl DTT solution (100 mM), 10 μl 5×RT-PCR buffer, 1 μl enzyme mixture, and 28.5 μl sterile distilled water may be subjected to the conditions such as reverse transcription at 60° C. for 30 minutes followed by 35 cycles of denaturation at 94° C. for 2 minutes, annealing at 60° C. for 2 minutes, and extension at 68° C. for 2 minutes. The RT-PCR analysis may be repeated twice to ensure reproducibility, for a total of three independent experiments.

Another embodiment of the method for diagnosing the diseases associated with the deficiency of GAK is performed by detecting the nucleotide sequence of GAK1 or GAK2 variant of the invention which comprises the steps of: (1) extracting total RNA from a sample obtained from the mammal; (2) amplifying the RNA by reverse transcriptase-polymerase chain reaction (RT-PCR) to obtain a cDNA sample; (3) bringing the cDNA sample into contact with the nucleic acid selected from the group consisting of SEQ ID NOs: 1 and 3, and the fragments thereof; and (4) detecting whether the cDNA sample hybridizes with the nucleic acid of SEQ ID NOs: 1 or 3, or the fragments thereof. If necessary, the amount of hybridized sample may be detected.

The expression of gene variants can be analyzed using Northern Blot hybridization approach. Specific fragment comprising nucleotides 957 to 958 of SEQ ID NO: 1 or nucleotides 119 to 124 of SEQ ID NO: 3 may be amplified by polymerase chain reaction (PCR) using primer set designed for RT-PCR. The amplified PCR fragment may be labeled and serve as a probe to hybridize the membranes containing total RNAs extracted from the samples under the conditions of 55° C. in a suitable hybridization solution for 3 hours. Blots may be washed twice in 2×SSC, 0.1% SDS at room temperature for 15 minutes each, followed by two washes in 0.1×SSC and 0.1% SDS at 65° C. for 20 minutes each. After these washes, blot may be rinsed briefly in suitable washing buffer and incubated in blocking solution for 30 minutes, and then incubated in suitable antibody solution for 30 minutes. Blots may be washed in washing buffer for 30 minutes and equilibrated in suitable detection buffer before detecting the signals. Alternatively, the presence of gene variants (cDNAs or PCR) can be detected using microarray approach. The cDNAs or PCR products corresponding to the nucleotide sequences of the present invention may be immobilized on a suitable substrate such as a glass slide. Hybridization can be preformed using the labeled mRNAs extracted from samples. After hybridization, nonhybridized mRNAs are removed. The relative abundance of each labeled transcript, hybridizing to a cDNA/PCR product immobilized on the microarray, can be determined by analyzing the scanned images.

According to the present invention, the method for diagnosing the diseases associated with the gene variants (GAK1 and GAK2) of the invention may also be performed by detecting the polypeptides of the gene variants. For instance, the polypeptides in protein samples obtained from the mammal may be determined by, but is not limited to, the immunoassay wherein the antibody specifically binding to the polypeptides of the invention is contacted with the protein samples, and the antibody-polypeptide complex is detected. If necessary, the amount of the antibody-polypeptide complexes can be determined.

The polypeptides of the gene variants may be expressed in prokaryotic cells by using suitable prokaryotic expression vectors. The cDNA fragments of GAK1 and GAK2 genes encoding the amino acid coding sequence may be PCR amplified with restriction enzyme digestion sites incorporated in the 5' and 3' ends, respectively. The PCR products can then be enzyme digested, purified, and inserted into the corresponding sites of prokaryotic expression vector in-frame to generate recombinant plasmids. Sequence fidelity of this recombinant DNA can be verified by sequencing. The prokaryotic recombinant plasmids may be transformed into host cells (e.g., *E. coli* BL21 (DE3)). Recombinant protein synthesis may be stimulated by the addition of 0.4 mM isopropylthiogalactoside (IPTG) for 3 hours. The bacterially-expressed proteins may be purified.

The polypeptides of GAK1 and GAK2 may be expressed in animal cells by using eukaryotic expression vectors. Cells may be maintained in Dulbecco's modified Eagle's medium (DMEM) supplemented with 10% fetal bovine serum (FBS; Gibco BRL) at 37° C. in a humidified 5% $CO_2$ atmosphere. Before transfection, the nucleotide sequence of each of the gene variant may be amplified with PCR primers containing restriction enzyme digestion sites and ligated into the corresponding sites of eukaryotic expression vector in-frame. Sequence fidelity of this recombinant DNA can be verified by sequencing. The cells may be plated in 12-well plates one day before transfection at a density of $5\times10^4$ cells per well. Transfections may be carried out using Lipofectamine Plus transfection reagent according to the manufacturer's instructions (Gibco BRL). Three hours following transfection, medium containing the complexes may be replaced with fresh medium. Forty-eight hours after incubation, the cells may be scraped into lysis buffer (0.1 M Tris HCl, pH 8.0, 0.1% Triton X-100) for purification of expressed proteins. After these proteins are purified, monoclonal antibodies against these purified proteins (GAK1 and GAK2) may be generated using hybridoma technique according to the conventional methods (de StGroth and Scheidegger, (1980) J Immunol Methods 35:1–21; Cote et al. (1983) Proc Natl Acad Sci USA 80: 2026–30; and Kozbor et al. (1985) J Immunol Methods 81:31–42).

According to the present invention, the presence of the polypeptides of the gene variants in samples of normal lung and lung cancers may be determined by, but is not limited to, Western blot analysis. Proteins extracted from samples may be separated by SDS-PAGE and transferred to suitable membranes such as polyvinylidene difluoride (PVDF) in transfer buffer (25 mM Tris-HCl, pH 8.3, 192 mM glycine, 20% methanol) with a Trans-Blot apparatus for 1 hour at 100 V (e.g., Bio-Rad). The proteins can be immunoblotted with specific antibodies. For example, membrane blotted with extracted proteins may be blocked with suitable buffers such as 3% solution of BSA or 3% solution of nonfat milk powder in TBST buffer (10 mM Tris-HCl, pH 8.0, 150 mM NaCl, 0.1% Tween 20) and incubated with monoclonal antibody directed against the polypeptides of gene variants. Unbound antibody is removed by washing with TBST for 5×1 minutes. Bound antibody may be detected using commercial ECL Western blotting detecting reagents.

The following examples are provided for illustration, but not for limiting the invention.

EXAMPLES

Analysis of Human Lung EST Databases

Expressed sequence tags (ESTs) generated from the large-scale PCR-based sequencing of the 5'-end of human lung (normal and large cell lung cancer) cDNA clones were compiled and served as EST databases. Sequence comparisons against the nonredundant nucleotide and protein databases were performed using BLASTN and BLASTX programs (Altschul et al., (1997) Nucleic Acids Res. 25: 3389–3402; Gish and States, (1993) Nat Genet 3:266–272), at the National Center for Biotechnology Information (NCBI) with a significance cutoff of $p<10^{-10}$. ESTs representing putative GAK encoding gene were identified during the course of EST generation.

Isolation of cDNA Clones

Two cDNA clones exhibiting EST sequences similar to the GAK gene were isolated from the lung cDNA libraries and named GAK1 and GAK2. The inserts of these clones were subsequently excised in vivo from the λZAP Express vector using the ExAssist/XLOLR helper phage system (Stratagene). Phagemid particles were excised by coinfecting XL1-BLUE MRF' cells with ExAssist helper phage. The excised pBluescript phagemids were used to infect *E. coli* XLOLR cells, which lack the amber suppressor necessary for ExAssist phage replication. Infected XLOLR cells were selected using kanamycin resistance. Resultant colonies contained the double stranded phagemid vector with the cloned cDNA insert. A single colony was grown overnight in LB-kanamycin, and the DNA was purified using a Qiagen plasmid purification kit.

Full Length Nucleotide Sequencing and Database Comparisons

Phagemid DNA was sequenced using the Epicentre#SE9101LC SequiTherm EXCEL™II DNA Sequencing Kit for 4200S-2 Global NEW $IR^2$ DNA sequencing system (LI-COR). Using the primer-walking approach, full-length sequence was determined. Nucleotide and protein searches were performed using BLAST against the non-redundant database of NCBI.

In Silico Tissue Distribution Analysis

The coding sequence for each cDNA clones was searched against the dbEST sequence database (Boguski et al., (1993) Nat Genet. 4: 332–3) using the BLAST algorithm at the NCBI website. ESTs derived from each tissue were used as a source of information for transcript tissue expression analysis. Tissue distribution for each isolated cDNA clone was determined by ESTs matching that particular sequence variants (insertions or deletions) with a significance cutoff of $p<10^{-10}$.

REFERENCES

Altschul et al., Gapped BLAST and PSI-BLAST: a new generation of protein database search programs, Nucleic Acids Res, 25: 3389–3402, (1997).

Ausubel et al., Current protocols in Molecular Biology, John Wiley & Sons, New York N.Y., ch. 9, 13, and 16, (1995).

Bates et al., Characterisation of human cyclin G1 and G2: DNA damage inducible genes. Oncogene, 13:1103–9, (1996).

Boguski et al., dbEST—database for "expressed sequence tags". Nat Genet. 4: 332–3, (1993).

Carney, D. N. The biology of lung cancer. Curr. Opin. Oncol. 4: 292–8, (1992a).

Carney, D. N. Biology of small-cell lung cancer. Lancet 339: 843–6, (1992b).

Cote et al., Generation of human monoclonal antibodies reactive with cellular antigens, Proc Natl Acad Sci USA 80: 2026–30 (1983).

de StGroth and Scheidegger, Production of monoclonal antibodies: strategy and tactics, J Immunol Methods 35:1–21, (1980).

Earley et al., Insight into the pathophysiology of restless legs syndrome. J Neurosci Res, 62:623–8, (2000).

Gish and States, Identification of protein coding regions by database similarity search, Nat Genet, 3:266–272, (1993).

Home et al., Cyclin G1 and cyclin G2 comprise a new family of cyclins with contrasting tissue-specific and cell cycle-regulated expression. J Biol Chem, 271:6050–61, (1996).

Hunter and Pines, Cyclins and cancer. Cell, 66:1071–4, (1991).

Ihde and Minna, Non-small cell lung cancer. Part II: Treatment. Curr. Probl. Cancer 15: 105–54, (1991).

Jiang et al., Amplification and expression of the human cyclin D gene in esophageal cancer. Cancer Res, 52:2980–3, (1992).

Kanaoka et al., GAK: a cyclin G associated kinase contains a tensin/auxilin-like domain. FEBS Lett, 402:73–80, (1997).

Keyomarsi and Pardee, Redundant cyclin overexpression and gene amplification in breast cancer cells. Proc Natl Acad Sci USA 90:1112–6, (1993).

Kimura et al., Structure, expression, and chromosomal localization of human GAK. Genomics 44:179–87, (1997).

Kohno et al., p53 mutation and allelic loss of chromosome 3p, 9p of preneoplastic lesions in patients with nonsmall cell lung carcinoma, Cancer 85: 341–7, (1999).

Kozak, An analysis of 5'-noncoding sequences from 699 vertebrate messenger RNAs. Nucleic Acids Res, 15: 8125–48, (1987).

Kozak, An analysis of vertebrate mRNA sequences: intimations of translational control, J Cell Biol, 115: 887–903, (1991).

Kozbor et al., Specific immunoglobulin production and enhanced tumorigenicity following ascites growth of human hybridomas, J Immunol Methods, 81:31–42 (1985).

Lammie et al., D11S287, a putative oncogene on chromosome 11q13, is amplified and expressed in squamous cell and mammary carcinomas and linked to BCL-1. Oncogene, 6:439–44, (1991).

Liu et al., Silent mutation induces exon skipping of fibrillin-1 gene in Marfan syndrome. Nat Genet 16:328–9, (1997).

Lukas et al., Alternative and aberrant messenger RNA splicing of the mdm2 oncogene in invasive breast cancer. Cancer Res 61:3212–9, (2001).

Lundrigan and Kadner, Nucleotide sequence of the gene for the ferrienterochelin receptor FepA in *Escherichia coli.* Homology among outer membrane receptors that interact with TonB. J Biol Chem 261:10797–801, (1986).

Michelland et al., Comparison of chromosomal imbalances in neuroendocrine and non-small-cell lung carcinomas. Cancer Genet Cytogenet, 114:22–30, (1999).

Ogunnariwo and Schryvers, Characterization of a novel transferrin receptor in bovine strains of *Pasteurella multocida.* J Bacteriol, 183:890–6, (2001).

Okamoto and Beach, Cyclin G is a transcriptional target of the p53 tumor suppressor protein. EMBO J, 13:4816–22, (1994).

Reimer et al., CL, Altered regulation of cyclin G in human breast cancer and its specific localization at replication foci in response to DNA damage in p53+/+ cells. J Biol Chem, 274:11022–9, (1999).

Roberge et al., A strategy for a convergent synthesis of N-linked glycopeptides on a solid support. Science 269: 202–4, (1995).

Sambrook, J. Cold Spring Harbor Press, Plainview N.Y., ch. 4, 8, and 16–17.

Schramm et al., Nucleotide sequence of the colicin B activity gene cba: consensus pentapeptide among TonB-dependent colicins and receptors. J Bacteriol, 169:3350–7, (1987).

Sethi, Science, medicine, and the future. Lung cancer, BMJ, 314: 652–655, (1997)

Siffert et al., Association of a human G-protein beta3 subunit variant with hypertension. Nat Genet, 18:45–8, (1998).

Simpson A. J. G. EST Accession No. BI026835

Skotzko et al., Retroviral vector-mediated gene transfer of antisense cyclin G1 (CYCG1) inhibits proliferation of human osteogenic sarcoma cells. Cancer Res, 55:5493–8, (1995).

Smith et al., The p53-regulated cyclin G gene promotes cell growth: p53 downstream effectors cyclin G and Gadd45 exert different effects on cisplatin chemosensitivity. Exp Cell Res, 230:61–8, (1997).

Smyth et al., The impact of chemotherapy on small cell carcinoma of the bronchus. Q J Med, 61: 969–76, (1986).

Stallings-Mann et al., Alternative splicing of exon 3 of the human growth hormone receptor is the result of an unusual genetic polymorphism. Proc Natl Acad Sci USA 93:12394–9, (1996).

Strausberg, R. EST Accession No. BC008668, BE619037, BG333001, BG746688, BG821224

Tuomainen et al., Association between body iron stores and the risk of acute myocardial infarction in men. Circulation, 97:1461–6, (1998).

Weinberg E D, Iron depletion: a defense against intracellular infection and neoplasia. Life Sci, 50:1289–97, (1992).

Weinberg E D, The role of iron in cancer. Eur J Cancer Prev, 5:19–36, (1996).

Weinberg E D, Iron, infection and sudden infant death. Med Hypotheses, 56:731–4, (2001).

Weinstat-Saslow et al., Overexpression of cyclin D mRNA distinguishes invasive and in situ breast carcinomas from non-malignant lesions. Nat Med, 1:1257–60, (1995).

What is claimed is:

1. An isolated nucleic acid, which consists of the nucleotide sequence of SEQ ID NO: 1 or 3.

2. An expression vector comprising the nucleic acid of claim 1.

3. An isolated host cell transformed with the expression vector of claim 2.

4. A method for producing a polypeptide, which comprises the steps of:

(1) culturing the host cell of claim 3 under conditions suitable for the expression of a polypeptide comprising the amino acid sequence of SEQ ID NO: 2 or 4; and (2) recovering the polypeptide from the host cell culture.

* * * * *

UNITED STATES PATENT AND TRADEMARK OFFICE

CERTIFICATE OF CORRECTION

PATENT NO. : 7,186,537 B2
APPLICATION NO. : 11/208877
DATED : March 6, 2007
INVENTOR(S) : Ken-Shwo Dai It is certified that error appears in the above-identified patent and that said Letters Patent is hereby corrected as shown below:

On title page, insert -- (73) Assignee: Bioptik Technology, Inc., Hsinchu (TW) --.

Signed and Sealed this

Ninth Day of October, 2007

JON W. DUDAS
*Director of the United States Patent and Trademark Office*

UNITED STATES PATENT AND TRADEMARK OFFICE

CERTIFICATE OF CORRECTION

PATENT NO. : 7,186,537 B2
APPLICATION NO. : 11/208877
DATED : March 6, 2007
INVENTOR(S) : Ken-Shwo Dai It is certified that error appears in the above-identified patent and that said Letters Patent is hereby corrected as shown below:

On title page, insert -- (73) Assignee: Bioptik Technology, Inc., Hsinchu (TW) --.

Signed and Sealed this

Thirtieth Day of October, 2007

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 2173
<212> TYPE: DNA
<213> ORGANISM: Homo sapiens
<220> FEATURE:
<221> NAME/KEY: CDS
<222> LOCATION: (128)..(574)
<223> OTHER INFORMATION:

<400> SEQUENCE: 1

cacgcccccg tccagcccca gcgtcggagg ggtgccctgg agggcgcggc tcaactccat      60

caagaacagc tttctgggct caccccgctt ccaccgccgg aaactgcaag ttccgacgcc     120

ggaggag atg tcc aac ctg aca cca gag tcg tcc cca gag ctg gcg aag      169
        Met Ser Asn Leu Thr Pro Glu Ser Ser Pro Glu Leu Ala Lys
        1               5                   10
```

-continued

```
aag tcc tgg ttt ggg aac ttc atc agc ctg gag aag gag gag cag atc      217
Lys Ser Trp Phe Gly Asn Phe Ile Ser Leu Glu Lys Glu Glu Gln Ile
15                  20                  25                  30

ttc gtg gtc atc aaa gac aaa cct ctg agc tcc atc aag gct gac atc      265
Phe Val Val Ile Lys Asp Lys Pro Leu Ser Ser Ile Lys Ala Asp Ile
                35                  40                  45

gtg cac gcc ttc ctg tcg att ccc agt ctc agc cac agc gtc atc tcc      313
Val His Ala Phe Leu Ser Ile Pro Ser Leu Ser His Ser Val Ile Ser
            50                  55                  60

caa acg agc ttc cgg gcc gag tac aag gcc acg ggg ggg cca gcc gtg      361
Gln Thr Ser Phe Arg Ala Glu Tyr Lys Ala Thr Gly Gly Pro Ala Val
        65                  70                  75

ttc cag aag ccg gtc aag ttc cag gtt gat atc acc tac acg gag ggt      409
Phe Gln Lys Pro Val Lys Phe Gln Val Asp Ile Thr Tyr Thr Glu Gly
    80                  85                  90

ggg gag gcg cag aag gag aac ggc atc tac tcc gtc acc ttc acc ctg      457
Gly Glu Ala Gln Lys Glu Asn Gly Ile Tyr Ser Val Thr Phe Thr Leu
95                  100                 105                 110

ctc tca ggc ccc agc cgt cgc ttc aag agg gtg gtg gag acc atc cag      505
Leu Ser Gly Pro Ser Arg Arg Phe Lys Arg Val Val Glu Thr Ile Gln
                115                 120                 125

gcc cag ctg ctg agc aca cac gac ccc ctg cgg ccc agc act tgt cag      553
Ala Gln Leu Leu Ser Thr His Asp Pro Leu Arg Pro Ser Thr Cys Gln
            130                 135                 140

aca cca cta act gta tgg aaa tgatgacggg gcggctttcc aaatgaatta         604
Thr Pro Leu Thr Val Trp Lys
        145

tcccgaaaag ttaacatgtc acctccacga ggccatcctc tgtgaccgaa ggcagctgct    664

gcggacccgc cctccctccg ctcctgctgt tgctgccggg cagtgaggcc cagcccagcg    724

ccccgtccac cccgcggcag ctcctcgcct cagctccgca cggcccgtgg gaggaaggcc    784

aggctcgggg gagcctcctc cagcccggcc gacccggact cccggtcacc tgacccctca    844

gcaagaacag ctgcctcccg tcctctcgtc tcacccgcgc ctcccttgcc tcatctgggg    904

cggctgtggg ctctggcgct cctctctggc tgaggtggaa acagagacac cctgtggcac    964

cagagccttc ccagcaggcc aggccgctgg gctgggatca gtgttattta tttgccgttt   1024

taatttatgg attctccgca cctctgttca gggaagggcg gcggccacat cccctgccgt   1084

ctgcgcgtct caggcagtgg gggggctggg gccagggcgc cctctgagga cagagctggt   1144

ggggcgcggg ggggctggcg agctactgta aactttaaag aattcctgca agatattttt   1204

ataaactttt ttttcttggt ggtttttgga aaagggtgtg gggtggggg cgccgctggg    1264

gcagggccag gttttgtgtt ttagtccctt gctcctgctt ctttctacac acacatctaa   1324

agacggtgcg gctcgctctg tcatgggttc cgtctctctc tgtggagaag cagctccacc   1384

tctggggggg ctcggggcag aggggcggtg tctcgtagcg ggcggcagcg ccagtccccc   1444

tctgtcaggc tggggcaatc ttggttttgt gtccaaaggt gaaggggtag gaggagggcc   1504

ctcagctggc cctccccaca cacaggacgg caggggcact gtgaggcttt tcttattaaa   1564

atgaaaaaat tgaaaaaaaa ggacaaagag tcggtggcgc tcctctgcag ggcgttctgt   1624

gcagagcgag gcccagggcg cactcaggag ggctcaggcc accctgccca gtgcccgccg   1684

ccgtgcttca ccccagctcc agcttctgtg ttcccttccg cccatgtgcc cagccctccc   1744

aggcgggcac agcccgggtg cggcggccgt gggggacggc gggtctgatg catgcctctg   1804

ccatggagtc gtctgtctgc ttcggtgcct gcccctgcct cccacccacc tcgtgtatag   1864

attttaacgc ttctgttaac attagacctc tgccacaggc tgggatttct atacataaga   1924
```

-continued

```
acaaaagcaa acacctagga cagcaaacgc caggcggtac aggcgggaag gggctctcca   1984

cggagatcga ggacacgaag caaactgcct cttgcttgcc ttccccttt gtgcttcgga   2044

cacacgcgga ctccagcagg cgccacggaa atgggcaagc cctgcagtg taccccctgtc   2104

ataactgtga gcagctgcag ctccggaaca ataaatccct tccgcaaaga caaaaaaaaa   2164

aaaaaaaaa                                                           2173


<210> SEQ ID NO 2
<211> LENGTH: 149
<212> TYPE: PRT
<213> ORGANISM: Homo sapiens

<400> SEQUENCE: 2

Met Ser Asn Leu Thr Pro Glu Ser Ser Pro Glu Leu Ala Lys Lys Ser
1               5                   10                  15

Trp Phe Gly Asn Phe Ile Ser Leu Glu Lys Glu Glu Gln Ile Phe Val
            20                  25                  30

Val Ile Lys Asp Lys Pro Leu Ser Ser Ile Lys Ala Asp Ile Val His
        35                  40                  45

Ala Phe Leu Ser Ile Pro Ser Leu Ser His Ser Val Ile Ser Gln Thr
    50                  55                  60

Ser Phe Arg Ala Glu Tyr Lys Ala Thr Gly Gly Pro Ala Val Phe Gln
65                  70                  75                  80

Lys Pro Val Lys Phe Gln Val Asp Ile Thr Tyr Thr Glu Gly Gly Glu
                85                  90                  95

Ala Gln Lys Glu Asn Gly Ile Tyr Ser Val Thr Phe Thr Leu Leu Ser
            100                 105                 110

Gly Pro Ser Arg Arg Phe Lys Arg Val Val Glu Thr Ile Gln Ala Gln
        115                 120                 125

Leu Leu Ser Thr His Asp Pro Leu Arg Pro Ser Thr Cys Gln Thr Pro
    130                 135                 140

Leu Thr Val Trp Lys
145
```